United States Patent
Everett et al.

(10) Patent No.: US 7,126,693 B2
(45) Date of Patent: Oct. 24, 2006

(54) SIMPLE HIGH EFFICIENCY OPTICAL COHERENCE DOMAIN REFLECTOMETER DESIGN

(75) Inventors: Matthew J. Everett, Livermore, CA (US); Yan Zhou, Pleasanton, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 312 days.

(21) Appl. No.: 10/811,748

(22) Filed: Mar. 29, 2004

(65) Prior Publication Data

US 2005/0213103 A1 Sep. 29, 2005

(51) Int. Cl.
*G01B 9/00* (2006.01)
(52) U.S. Cl. .................. 356/479; 356/497; 356/369
(58) Field of Classification Search ............. 356/479, 356/497, 491, 493
See application file for complete search history.

(56) References Cited

U.S. PATENT DOCUMENTS

| | | | |
|---|---|---|---|
| 5,202,745 A | 4/1993 | Sorin et al. | 356/73.1 |
| 5,321,501 A | 6/1994 | Swanson et al. | 356/345 |
| 5,459,570 A | 10/1995 | Swanson et al. | 356/345 |
| 5,883,717 A | 3/1999 | DiMarzio et al. | 356/351 |
| 6,111,645 A | 8/2000 | Tearney et al. | 356/354 |
| 6,282,011 B1 | 8/2001 | Tearney et al. | 359/287 |
| 6,377,349 B1 | 4/2002 | Fercher | 356/450 |
| 6,385,358 B1 | 5/2002 | Everett et al. | 385/12 |
| 6,657,727 B1 | 12/2003 | Izatt et al. | 356/450 |
| 6,961,123 B1 * | 11/2005 | Wang et al. | 356/364 |
| 2002/0093655 A1 * | 7/2002 | Everett et al. | 356/369 |
| 2005/0036150 A1 * | 2/2005 | Izatt et al. | 356/479 |
| 2005/0140984 A1 | 6/2005 | Hitzenberger | 356/497 |

FOREIGN PATENT DOCUMENTS

EP   1 253 398 A1   10/2002

OTHER PUBLICATIONS

J.G. Fujimoto et al., "Optical Coherence Tomography: An Emerging Technology for Biomedical Imaging and Optical Biopsy," *Neoplasia*, vol. 2, Nos. 1-2, Jan.-Apr. 2000, pp. 9-25.
J.G. Fujimoto, "Optical coherence tomography for ultrahigh resolution *in vivo*, imaging," *Nature Biotechnology*, vol. 21, No. 11, Nov. 2003, pp. 1361-1367.
D. Huang et al., "Optical Coherence Tomography," *Science*, vol. 254, Nov. 22, 1991, pp. coversheet and 1178-1181.
A.D. Kersey et al., "Polarisation-Insensitive Fibre Optic Michelson Interferometer," *Electronics Letters*, vol. 27, No. 6, Mar. 14, 1991, pp. 518-520.

(Continued)

*Primary Examiner*—Gregory J. Toatley, Jr.
*Assistant Examiner*—Denise B Anderson
(74) *Attorney, Agent, or Firm*—Stallman & Pollock LLP

(57) ABSTRACT

The present invention discloses simple and yet highly efficient configurations of optical coherence domain reflectometry systems. The combined use of a polarizing beam splitter with one or two polarization manipulator(s) that rotate the returned light wave polarization to an orthogonal direction, enables one to achieve high optical power delivery efficiency as well as fixed or predetermined output polarization state of the interfering light waves reaching a detector or detector array, which is especially beneficial for spectral domain optical coherence tomography. In addition, the system can be made insensitive to polarization fading resulting from the birefringence change in the sample and reference arms. Dispersion matching can also be easily achieved between the sample and the reference arm for high resolution longitudinal scanning.

69 Claims, 9 Drawing Sheets

(Embodiment 1)

OTHER PUBLICATIONS

M. Kobayashi et al., "Polarization-Independent Interferometric Optical-Time-Domain Reflectometer," *Journal of Lightwave Technology*, vol. 9, No. 5, May 1991, pp. 623-628.

A.M. Rollins et al., "Emerging Clinical Applications of Optical Coherence Tomography," *Optics & Photonics News*, vol. 13, Issue 4, Apr. 2002, pp. coversheet and 37-41.

A.M. Rollins et al., "Optimal interferometer designs for optical coherence tomography," *Optics Letters*, vol. 24, No. 21, Nov. 1, 1999, pp. 1484-1486.

J.M. Schmitt, "Optical Coherence Tomography (OCT): A Review," *IEEE Journal of Selected Topics in Quantum Electronics*, vol. 5, No. 4, Jul./Aug. 1999, pp. 1205-1215.

E.A. Swanson et al., "Optical Coherence Tomography Principles, Instrumentation, and Biological Applications," *Biomedical Optical Instrumentation of Laser-Assisted Biotechnology*, A.M. Verga Scheggi et al. (eds.), 1996 Kluwer Academic Publishers, printed in the Netherlands, pp. 291-303.

A.B. Vakhtin et al., "Differential spectral interferometry: an imaging technique for biomedical applications," *Optics Letters*, vol. 28, No. 15, Aug. 1, 2003, pp. 1332-1334.

R.C. Youngquist et al., "Optical coherence-domain reflectometry: a new optical evaluation technique," *Optics Letters*, vol. 12, No. 3, Mar. 1987, pp. 158-160.

\* cited by examiner

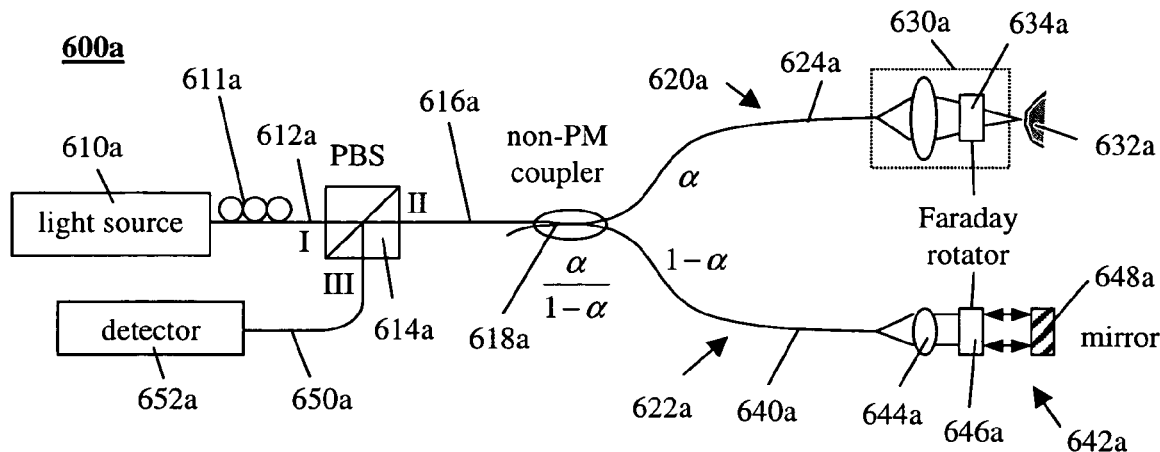
Fig. 6A (Embodiment 1)
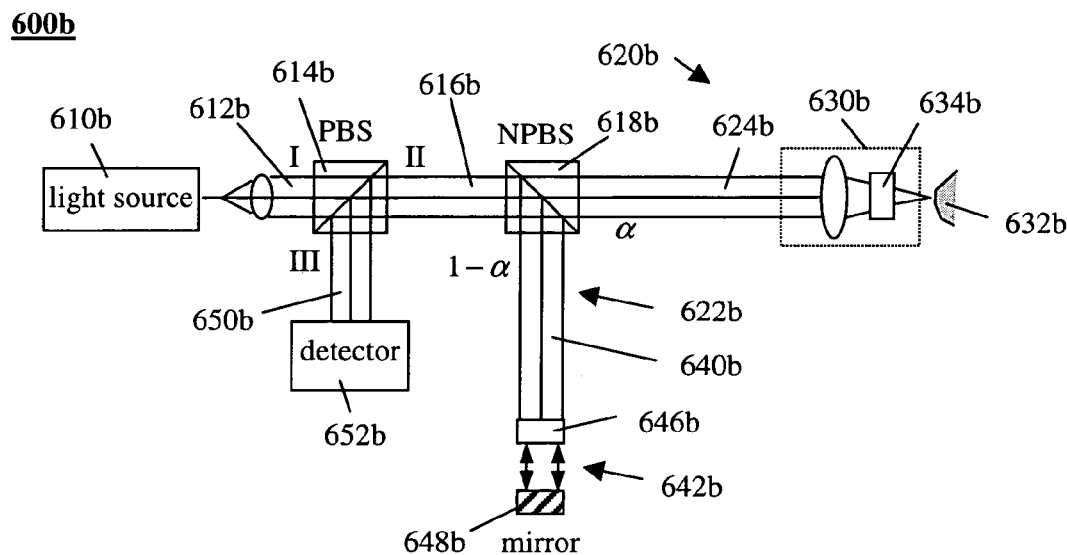
Fig. 6B (Embodiment 1)

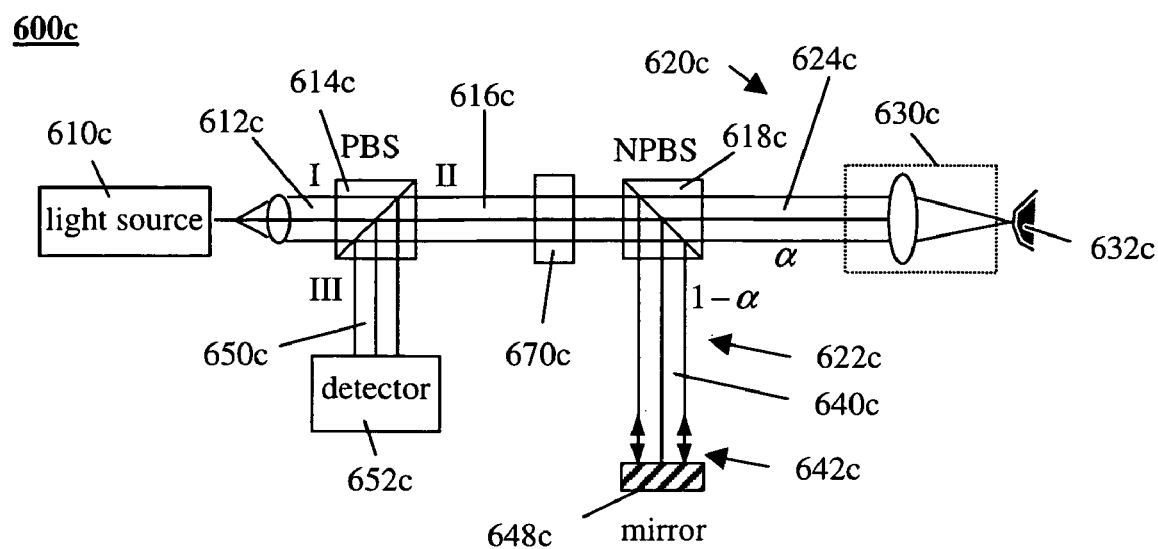
Fig. 6C (Embodiment 1)

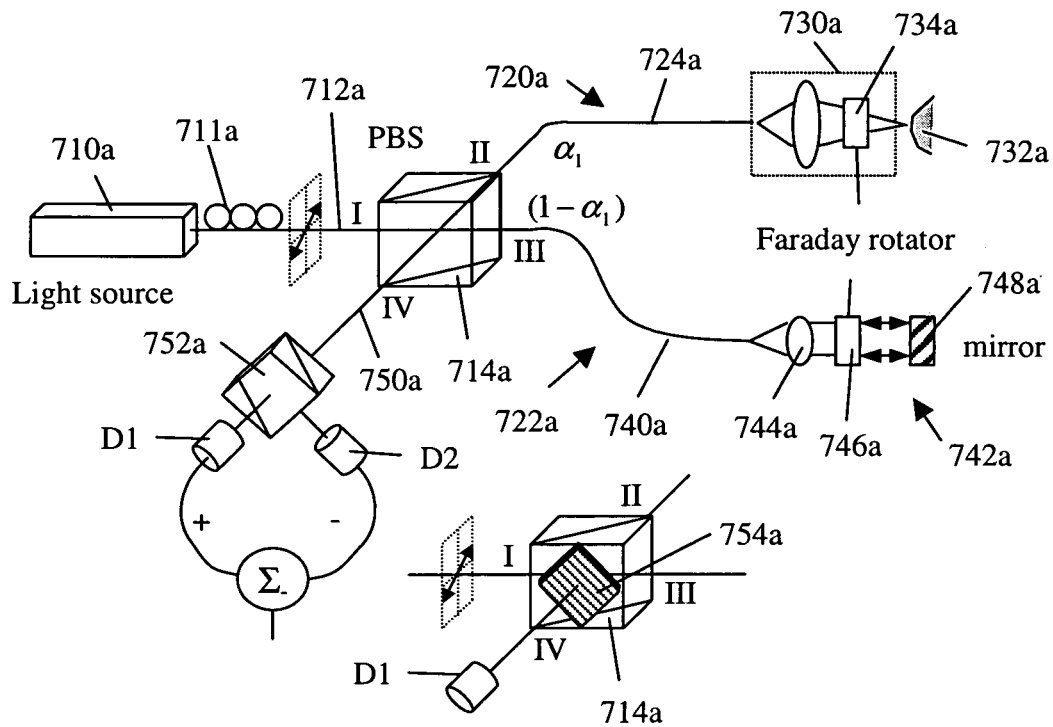
Fig. 7A (Embodiment 2)
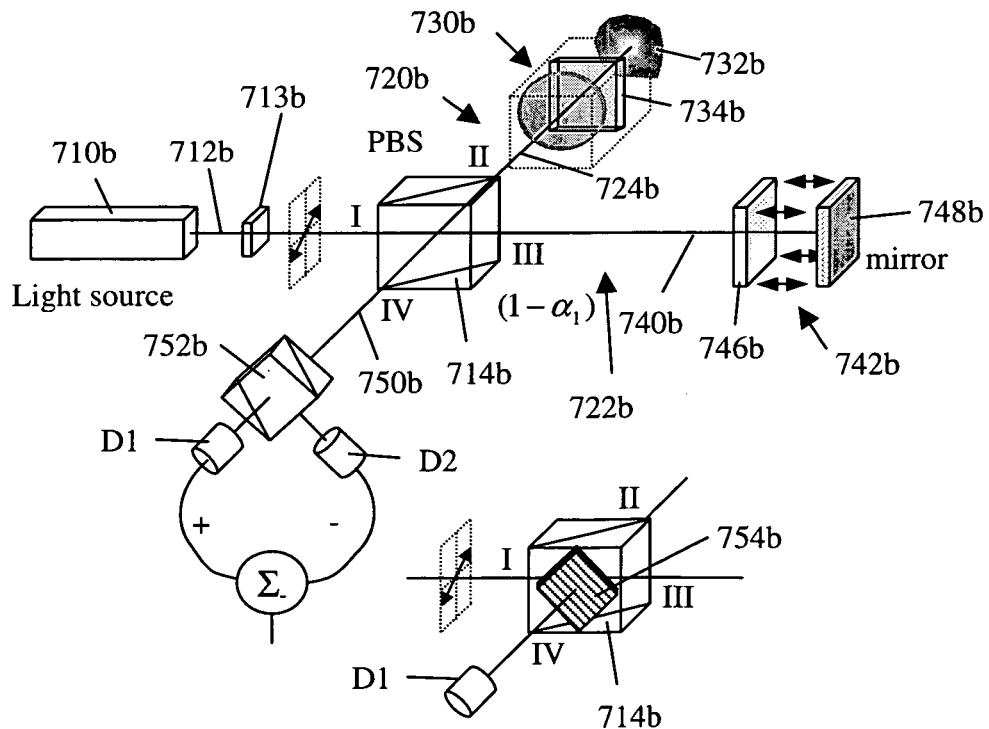
Fig. 7B (Embodiment 2)

SIMPLE HIGH EFFICIENCY OPTICAL COHERENCE DOMAIN REFLECTOMETER DESIGN

BACKGROUND OF THE INVENTION

1. Field of the Invention

The invention relates generally to optical imaging and in particular to systems and methods for achieving flexibility in interference fringe visibility control and optimization of signal to noise ratio, as well as for achieving polarization insensitivity, dispersion matching and optical output polarization control in optical coherence domain reflectometry (OCDR) or optical coherence tomography (OCT).

2. Description of Related Art

Optical coherence domain reflectometry (OCDR) is a technique initially developed to provide a higher resolution over optical time domain reflectometry (OTDR) for the characterization of the position and the magnitude of reflection sites in such optical assemblies as optical fiber based systems, miniature optical components and integrated optics (Youngquist et al., "Optical Coherence-Domain Reflectometry: A New Optical Evaluation Technique", 1987, Optics Letters 12(3):158–160). With the addition of transverse scanning, this technique has been widely and successfully extended to the imaging of biological tissues, and is termed optical coherence tomography (OCT) (Huang, D., E. A. Swanson, et al. (1991). "Optical coherence tomography." Science 254 1178–81; and U.S. Pat. Nos. 5,321,501 and 5,459,570). Since then, a large number of applications have been found for this technology as evidenced by a number of review articles (Swanson E. A. et al. "Optical coherence tomography, Principles, instrumentation, and biological applications" Biomedical Optical Instrumentation and Laser-Assisted Biotechnology, A. M. Verga Scheggi et al. (eds.) pages: 291–303, 1996 Kluwer Academic Publishers, Printed in the Netherlands; Schmitt, J. M. "Optical coherence tomography (OCT): a review" IEEE Journal of Selected Topics in Quantum Electronics, Volume: 5, Issue: 4, Year: July/August 1999, pages: 1205–1215; Fujimoto, J. G. et al. "Optical Coherence Tomography: An Emerging Technology for Biomedical Imaging and Optical Biopsy" Neoplasia (2000) 2, 9–25; Rollins A. M. et al. "Emerging Clinical Applications of Optical Coherence Tomography" Optics and Photonics News, Volume 13, Issue 4, 36–41, April 2002; Fujimoto, J. G. "Optical coherence tomography for ultrahigh resolution in vivo imaging." Nat Biotechnol 21(11): 1361–7, (2003)). Each of these documents is incorporated herein by reference.

The most straightforward and most commonly used interferometer configuration for OCDR or OCT is a standard Michelson interferometer. As shown in FIG. 1, light from a low coherence source 110 is input into a beam splitter or 2×2 fiber optic coupler 112, where the light is split and directed into a sample arm 114 and a reference arm 116. An optical fiber 118 in the sample arm 114 extends into a device 120 that scans an object 122. The reference arm 116 provides a variable optical delay. Light input into the reference arm 116 is reflected back by a reference mirror 124. A piezoelectric modulator 126 may be included in the reference arm 116 with a fixed reference mirror 124, or the modulator 126 may be eliminated by scanning the mirror 124 in the Z-direction. The reflected reference beam from reference arm 116 and the scattered sample beam from sample arm 114 pass back through the coupler 112 to detector 128 (including processing electronics), which processes the signals by techniques that are known in the art to produce a backscatter profile or image on a display unit 130.

This configuration is advantageous in that it uses a minimum number of optical components and is hence the simplest. It can be implemented using bulk or fiber optics or a combination thereof. However, this configuration is limited to an optical efficiency of 25% as explained below.

By examining the configuration, it is not difficult to discover that the optical power reaching the detector from the two arms is reciprocal with respect to the beam splitter or fiber coupler (BS/FC). Assuming that the power split ratio of the beam splitter is $$\frac{\alpha}{1-\alpha}$$

and neglecting loss in the splitter, the attenuation by the beam splitter or the fiber coupler (BS/FC) to both the sample optical wave and the reference optical wave is the same and is equal to $\alpha(1-\alpha)$, the only difference is that for one wave it will propagate straight-through the BS/FC first with an attenuation by a factor of $\alpha$ and then crossover the BS/FC with a further attenuation by a factor of $(1-\alpha)$, whereas for the other wave, it will crossover the BS/FC first with an attenuation by a factor of $(1-\alpha)$ and then propagate straight-through the BS/FC with a further attenuation by a factor of $\alpha$. It is well known to those skilled in the art that for such a configuration, the most efficient power splitting ratio is 50/50, where $$\frac{\alpha}{1-\alpha} = 1,$$

simply because the function $\alpha(1-\alpha)$ has its maximum value when $\alpha=0.5$. For example, with a 50/50 power split ratio, for either the sample arm or the reference arm, the optical power is firstly attenuated at the BS/FC by 50% from the light source to the sample or reference arm and then further attenuated by 50% from the sample or reference arm to the detector, which leads to a total overall power attenuation factor of 50%×50%=25% for both arms. If the BS/FC power split ratio is 90/10, then for the reference and the sample arm respectively, the total overall power attenuation factor by the BS/FC will be 90%×10% and 10%×90%, which is the same and is equal to only 9%.

Various configurations have been proposed to improve the optical power efficiency. The configuration described in this patent is simpler than those previously proposed designs and also addresses polarization fading issues that are not addressed by the other high optical efficiency designs.

Rollins and Izatt (U.S. Pat. No. 6,657,727; Andrew M. Rollins, Joseph A. Izatt "Optimal interferometer designs for optical coherence tomography" Optics Letters, Vol. 24, Issue 21, Page 1484 (1999)) proposed a number of interferometer configurations to improve the optical efficiency of the above Michelson interferometer configuration. As shown in FIG. 2, a key optical element that is used in all their configurations is a commercially available non-reciprocal device called an optical circulator and such a circulator is combined with unbalanced couplers, and (or) balanced heterodyne detection for optical power efficient interferometer construction. In contrast, the design we describe herein eliminates the optical circulator, a complex and expensive component. Our design is also very compact and relatively low cost as it uses a minimum number of optical elements.

It should be pointed out that FIG. 2 encompasses six configurations, where the three insets (FIGS. 2Aii; 2Bii and 2Cii) basically show a modification from the three corresponding balanced heterodyne detection approach employing balanced couplers to a single detector based detection employing unbalanced coupler(s) as shown in the main FIGS. 2Ai; 2Bi and 2Ci. Refer now to the first two configurations (FIGS. 2Ai and 2Aii), which are based on a Mach-Zehnder interferometer with the sample 222 located in a sample arm 214 and the reference optical delay line (ODL) 225 in the reference arm 216. In the case of 2Ai, the main difference from a standard Mach-Zehnder interferometer is that the prior fiber coupler 212 has an optical power split ratio of $$\frac{\alpha_1}{1-\alpha_1}$$

instead of 50/50 that is optimized for optical power efficient high SNR detection by directing most of the original optical power to the sample arm 214 and meanwhile light is coupled to the sample 222 through an optical circulator 232 such that the backscattered optical signal is collected by the delivery fiber 218 but is redirected to the post fiber coupler 234. The reference arm ODL 225 may be transmissive using, for example, a fiber wrapped PZT based fiber stretcher or it may be retroreflective using, for example, a corner mirror or cube combined with another optical circulator (not shown, see U.S. Pat. No. 6,657,727). Note that in FIG. 2Ai, the post fiber coupler 234 has a split ratio of 50/50 and due to the employment of balanced heterodyne detection 236, Izatt and Rollin showed that the SNR of FIG. 2Ai can be improved over that of a standard Michelson configuration as shown in FIG. 1.

In the configuration of FIG. 2Aii, the post fiber coupler 238 is also made non-50/50 and a single detector 240 is used. The advantage of FIG. 2Aii embodiment as compared to FIG. 2Ai embodiment is that since only one detector is used, the cost of the system will be lower than that of FIG. 2Ai.

Refer now to FIGS. 2Bi and 2Bii, while the sample arm part is the same as in FIGS. 2Ai and 2Aii, the reference arm ODL 242 is made retroreflective but without the need of a second optical circulator. Again, the optical power split ratio of both the prior fiber coupler 244 and the post fiber coupler 246, $$\frac{\alpha_1}{1-\alpha_1} \text{ and } \frac{\alpha_2}{1-\alpha_2},$$

can be properly chosen for either the two detector based balanced heterodyne detection case 248 or the unbalanced single detector case 250 to optimize the SNR such that the system is optical power efficient. Izatt and Rollin showed that the SNR improvement of the FIGS. 2Bi and 2Bii embodiment is very similar to that of FIGS. 2Ai and 2Aii embodiments. Note that there will be a small portion of the optical power from the reference ODL 242 being returned to the light source path.

The configurations of FIGS. 2Ci and 2Cii are basically Michelson interferometer based and their difference as compared to FIG. 1 is the use of an optical circulator 252 in between the light source 254 and the fiber coupler 256 to channel the returned light from the fiber coupler 256 initially propagating towards the light source 254 now completely to the detector, d2. While for balanced heterodyne detection, the optical power split ratio of the fiber coupler 256 must be made 50/50, it should be noted that for the case of a single detector unbalanced detection 258 (FIG. 2Cii), the optical power delivered to detector d2 from the sample arm 260 and the reference arm 262 can be made different or non-reciprocal since for detector d2, the sample optical signal will propagate straight-through the fiber coupler 256 twice and the reference optical signal will cross-over the fiber coupler 256 twice. As a result, the optical power delivery to detector d2 can be made efficient by properly selecting the fiber coupler optical power split ratio $$\frac{\alpha}{1-\alpha}.$$

Izatt and Rollin stated that for the configuration shown in FIGS. 2Ci, the SNR can be improved over that of FIG. 1 and although this configuration is not as power efficient as the other two, i.e. FIGS. 2Ai and 2Bi, its significant advantage is that it can be easily retrofitted with a circulator in the source arm and with a balanced receiver, with no need to disturb the rest of the system. As for FIG. 2Cii, the SNR improvement is similar to that of FIGS. 2Aii and 2Bii.

As an extension to all their configurations, Izatt and Rollin included, in their patent (U.S. Pat. No. 6,657,727), three more configurations as shown in FIG. 3 in which a transmissive sample is in the place of the circulator and the sample. They defined a transmissive sample as any sample illumination and collection geometry in which the illumination and collection optics occupy separate optical paths. Such designs have significant alignment issues and are not relevant to the invention being described where the illumination and collection optics occupy the same optical path.

As can be seen from the above-mentioned various configurations, the key advantage of these prior configurations lies in the improvement of the optical power delivery efficiency to the detector(s), by properly selecting an optical power split ratio $$\frac{\alpha}{1-\alpha}$$

(for either the prior and/or the post fiber coupler).

Another issue with the classic Michelson interferometer (FIG. 1) is that light from the reference arm is coupled back into the optical source, causing side effects that can impact the quality of the resulting image. Most of the configurations proposed by Izatt and Rollins address this issue as does the invention described herein. An issue not addressed by Izatt and Rollins configurations above is polarization fading, or loss of signal associated with mismatches between the polarization states of the light from the reference and sample arms. These mismatches are caused by birefringence and its fluctuations in the sample and reference arms, generally dominated by the birefringence in the optical fibers.

For a retraced light wave, placement of Faraday rotators at the ends of the fibers has been shown in the prior art to eliminate polarization fading due to the fiber optic components. FIG. 4 shows the approach of using two Faraday rotator mirrors at the end of the two arms of a standard Michelson fiber optic interferometer to eliminate polarization fading (Kersey, A. D. et al. "Polarization-insensitive fiber optic Michelson interferometer", Electronics Letters, Volume: 27, Issue: 6, pages: 518–520, (1991)). In this design, the Faraday rotator and mirror enable birefringence compensation in a retraced fiber path for both the sample arm and the reference arm. Although this design solved the problem of polarization fading, it did not address the issue of optical efficiency as the optical splitter configuration is the same as the standard Michelson interferometer configuration of FIG. 1. The invention described herein takes advantage of the polarization rotation caused by the Faraday rotators to increase the optical efficiency of the system by introducing a polarizing beam splitter in the source arm for coupling the light returning toward the source into a detector. This leads to an unbalanced optical efficiency assuming no birefringence in the sample and the use of a polarized source. An additional advantage of such a system is that the light being collected on the detector is linearly polarized, which is advantageous for spectral domain optical coherence tomography and reflectometry systems.

In spectral domain OCT systems, the light is dispersed by a diffraction grating and collected by an array of detectors. The efficiency of the diffraction grating is generally polarization dependent, and thus can be made most efficient for linearly polarized light. As will be elaborated later, the present invention can meet such a requirement.

In order to partially address the polarization fading problem, U.S. Pat. No. 6,564,089 by Izatt et al. mentioned the provision of a polarization compensation means such as a Faraday rotator on the side of the light emission of the optical probe on top of some of the interferometer configurations as discussed before with respect to FIG. 2. By doing so, the OCT can obtain a stabilized interference output regardless of the state of the bend of the sample arm. The inclusion of a Faraday rotator at the end of the sample arm optical probe only is particularly related to the application of OCT to endoscopic biological imaging in which the sample arm optical probe beam needs to be rotated to acquire cross sectional images of a tubular tissue and hence the birefringence property of the sample arm is very vulnerable to fluctuations. A drawback of such a system is the additional cost of the Faraday rotator and furthermore, while polarization compensation is provided for the sample arm, the same is not provided for the reference arm and as a result, there will be a mismatch in the birefringence as well as the dispersion properties between the two arms. Obviously, any birefringence fluctuation in the reference arm will still cause polarization fading and at the same time, the final output optical polarization of the configuration is not predetermined and hence is not suitable for spectral domain OCT which is polarization dependent.

In terms of addressing the polarization fading issue, besides using Faraday rotators, an alternative approach is to use polarization-maintaining (PM) fibers. In addition, a so-called polarization diversity receiver (PDR) scheme (Sorin, et al. "Polarization independent optical coherence-domain reflectometry" U.S. Pat. No. 5,202,745) can also be used. There are also combinations in which PM-fiber, polarization control optical elements and FRM are used (Everett M. et al. "Birefringence insensitive optical coherence domain reflectometry system" U.S. Pat. No. 6,385,358). PM fibers have several issues associated with their two orthogonal polarization axes, which make them undesirable for commercial OCDR or OCT applications. These include variable optical dispersion, difficulties in maintaining high polarization extinction in the connection between two PM-fibers or between a PM-fiber and a polarization optical component, and high cost.

FIG. 5 shows Sorin, et al.'s polarization independent optical coherence-domain reflectometry configuration (U.S. Pat. No. 5,202,745), where the light returning from the sample and reference arms is split into two orthogonal polarization modes with each mode being detected by a separate detector. In this design, a linear polarizer in the reference arm is adjusted to compensate for birefringence in the reference arm so as to equal signal powers on each detector in the detector arm in the absence of a signal from the test, or sample, arm. The problem with this approach is that the polarizer needs to be adjusted as the birefringence in the reference arm changes. As the birefringence in the non-PM reference arm fiber is strongly affected by temperature and stress, the system must be recalibrated with each use, and suffers from polarization drift during use.

An alternate design for a fiber optic polarization insensitive OCDR system with non-PM fiber in the sample arm has previously been described (Kobayashi et al, "Polarization-Independent Interferometric Optical-Time-Domain Reflectometer", 1991, J. Lightwave Tech. 9(5):623–628). The reference arm in this system consists of all PM optical fiber. As the two arms use different types of optical fibers, their dispersion properties are drastically different, which hence will lead to loss of resolution due to mismatched dispersion between the sample and reference arms. The system also requires a specialized 50/50 coupler.

U.S. Pat. No. 6,385,358 disclosed a hybrid system involving the use of PM fibers, non-PM fibers and Faraday rotators. An important feature in this patent is the use of a 22.5° Faraday rotator in the beam path to enable a double path rotation of the polarized beam returned from reference arm so that the beam is equally split into two orthogonal polarization modes to interfere with the two corresponding but not necessarily equally split components of the beam from the sample arm, which are then detected by two detectors. By summing the interference signal envelops from the two detectors, the final signal is made independent of the birefringence of the sample arm in a similar way as in the case of a polarization diversity receiver. In addition to polarization insensitivity, the dispersion property of the sample arm is also matched with that of the reference arm to eliminate the dispersion effects that degrade image resolution. Furthermore, arbitrary power split ration $\alpha/(1-\alpha)$ fiber coupler is also used to enable high efficiency optical power delivery to the detector. Considering that for medical applications, the portion of the fiber optic interacting with the patient must be changed for hygienic reasons, a non-PM fiber is incorporated into the sample arm to accommodate a disposable section at the end of the sample arm that interacts with the sample. However, a major disadvantage of the disclosed designs is that the system configuration is not simple at all, as it involves length matched PM fiber and non-PM fiber between the sample and references arms, their splices or connections and the use of a relatively large number of various optical components such as (PM or non-PM) fiber coupler, free space polarization beam splitter (PBS), various Faraday rotators of different rotation angles, and two photodetectors. In the case of a 22.5° Faraday rotator which is placed between a single PM fiber and a single mode non-PM fiber, the light beam needs to be expanded from a first fiber, collimated, passed through the Faraday rotator, and then refocused into the other fiber. All of these make the system both quite complicated and also expensive.

Given the problems with the systems described above, there is obviously a need to combine the benefit of optical power delivery efficiency with polarization insensitivity as well as dispersion matching in a simply configuration that will lower the cost and enhance the performance. The present invention addresses the above-mentioned problems and significantly improves on the prior art systems by effectively achieving high optical power delivery efficiency, polarization insensitivity and also dispersion matching, in a more compact, more robust, and also less expensive manner.

SUMMARY OF THE INVENTION

The present invention discloses simple configurations of optical coherence domain reflectometry systems that are polarization insensitive and also highly efficient in terms of optical power delivery to the detector(s). In particular, a unique feature of the present invention is the combined use of a polarizing beam splitter with one or two polarization manipulator(s) that rotate the returned light wave polarization to an orthogonal direction. Such a combination provides the flexibility in interference fringe visibility control and the optimization of signal to noise ratio, as well as the possibility of polarization insensitivity, dispersion matching and optical output polarization control in an optical coherence domain reflectometry (OCDR) or optical coherence tomography (OCT) system.

In one aspect of the invention, an OCDR system (embodiment 1) includes a light source; a polarizing beam splitter having at least three ports; a non-polarizing beam splitter having at least three ports that is optically connected with the polarizing beam splitter; a sample arm leading to a sample that is optically connected to a first output port of the non-polarizing beam splitter; a reference arm leading to a reflector that is optically connected to a second output port of the non-polarizing beam splitter; one or two polarization manipulator(s) that rotate the returned polarization to an orthogonal direction, a detector that collects light combined by the non-polarizing beam splitter from the sample and reference arms, returned to the polarizing beam splitter in an orthogonal polarization state, and thus channeled by the polarizing beam splitter to the detector path for interference signal detection and processing.

Another aspect of the present invention is to provide a method for performing optical coherence domain reflectometry comprising the steps of: guiding a light beam through a polarizing beam splitter and a non-polarizing beam splitter into a sample arm leading to a sample, and a reference arm leading to a reflector; rotating the polarization direction of returned light waves from said sample and said reflector to an orthogonal direction, followed by combining said returned light waves in said non-polarizing beam splitter, or combining returned light waves from said sample and said reference reflector in said non-polarizing beam splitter, and rotating the polarization direction of said returned light waves to an orthogonal direction; guiding said returned light waves to said polarizing beam splitter; and channeling at said polarizing beam splitter said combined and returned light waves having an orthogonal polarization state to a detector for interference signal extraction and processing.

In another aspect of the present invention, an OCDR system (embodiment 2) is disclosed that includes a light source; a polarizing beam splitter having four ports, for receiving the light from said source through a first port, splitting the light into a second port and a third port, combining the light returned from the second port and third port, and channeling the combined light to a fourth port; a sample arm containing a polarization manipulator that rotates the returned light wave polarization to an orthogonal direction and a sample, wherein the sample arm is optically connected to the second port of the polarizing beam splitter; a reference arm containing a polarization manipulator that rotates the returned light wave polarization to an orthogonal direction and a reflector, wherein the reference arm is optically connected to the third port of the polarizing beam splitter; an analyzer for combining into a common polarization direction, two orthogonally polarized light waves, each from the sample and reference arms respectively, propagation-directionally combined and channeled by the polarizing beam splitter; and a detector (or two detectors) for collecting the polarization-direction-combined light for interference signal extraction.

Still another aspect of the present invention is to provide a method for performing optical coherence domain reflectometry comprising the steps of: guiding a light beam through a polarizing beam splitter into a sample arm containing a polarization manipulator that rotates the returned light wave polarization to an orthogonal direction and a sample, and a reference arm containing a polarization manipulator that rotates the returned light wave polarization to an orthogonal direction and a reflector; combining in the polarizing beam splitter, the returned light waves from the sample arm and the reference arm; channeling at the polarizing beam splitter, the combined and returned light waves having mutually orthogonal polarization states through the forth port to an analyzer and detector arm; projecting at the analyzer the two mutually orthogonally polarized light waves from the sample and reference arms respectively onto one (or two) polarization-passing-through-axis(es) of the analyzer; and collecting at the detector(s), the polarization-direction-combined interfering light wave(s) for interference signal extraction and processing.

An object of the invention is to achieve high optical power delivery efficiency, polarization insensitivity as well as dispersion matching at the same time in a simple reflective-arms-based optical interferometer configuration, and this is realized through a combined use of a polarizing beam splitter with one or two polarization manipulator(s) that rotates the returned light wave polarization to an orthogonal direction.

A second object of the invention is to achieve a predetermined or fixed polarization direction of the final combined interfering light waves at the detector or detection module so that a polarization sensitive detector or detection module can be used for such cases as spectral domain optical coherence tomography (SD-OCT).

A further object of the invention is to use non-PM fiber and non-PM fiber pigtailed fiber optic devices so that the cost of the system is much lower than PM fiber based counterparts.

Another object of the present invention is to make it possible to adjust the polarization direction of the light wave projecting onto the sample without causing polarization fading resulting from the birefringence changes in the sample arm.

Another object of the present invention is to make it possible to achieve optical path length delay or phase modulation using a fiber-wrapped PZT based transmissive optical delay line in the lead non-PM fiber portion of either the reference arm or the sample arm, without causing polarization fading resulting from the birefringence changes in the fiber portion of the reference or sample arm.

Another object of the present invention is to also provide a configuration (embodiment 2) that can be easily converted between a two-detector-based balanced heterodyne detection scheme and a one detector based unbalanced detection scheme.

Still another object of the invention is to further lower the cost of an OCDR system by using a thin film base analyzer to achieve the one detector based unbalanced detection scheme in embodiment 2.

These and other features and advantages of the present invention will become more readily apparent to those skilled in the art upon review of the following detailed description of the preferred embodiments taken in conjunction with the accompanying drawings.

BRIEF DESCRIPTION OF THE DRAWINGS

FIG. 6A shows a fiber optics version of a first embodiment of the presently invented interferometer configuration which is highly optical power efficient as well as polarization insensitive.

FIG. 6B shows a bulk optics version of a first embodiment of the presently invented interferometer configuration which is highly optical power efficient as well as polarization insensitive.

FIG. 6C shows a bulk optics version of a first embodiment of the presently invented interferometer configuration which uses only one polarization manipulator and is highly optical power efficient as well as polarization insensitive.

FIG. 7A shows a fiber optics version of a second embodiment of the presently invented interferometer configuration which is highly optical power efficient as well as polarization insensitive.

FIG. 7B shows a bulk optics version of a second embodiment of the presently invented interferometer configuration which is highly optical power efficient as well as polarization insensitive.

DETAILED DESCRIPTION OF THE INVENTION

Figure 1:
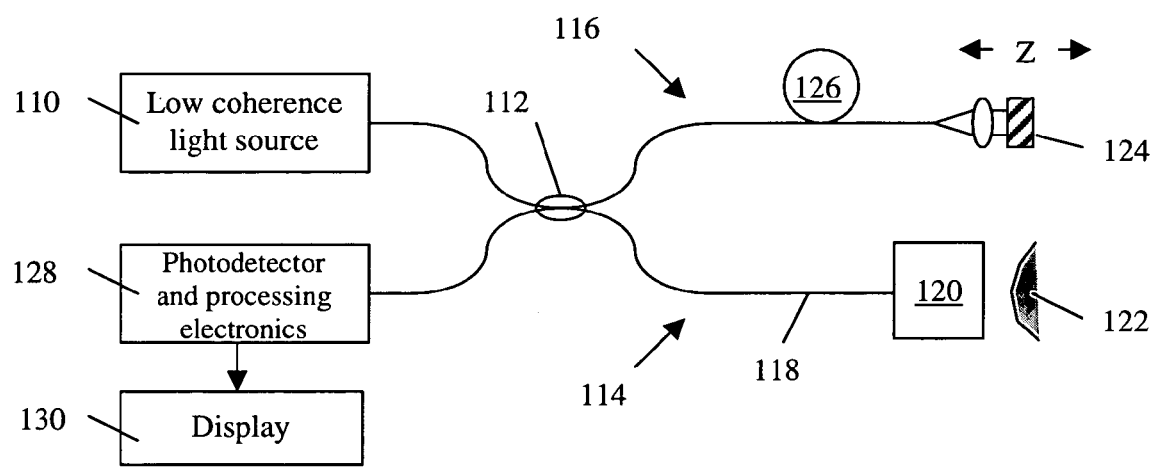
FIG. 1 shows a standard Michelson interferometer configuration used for OCDR or OCT.

The present invention is an optical coherence domain reflectometer (OCDR) system with a high optical power delivery efficiency and also fiber birefringence insensitivity that can use non-polarization maintaining (non-PM) fibers. Here, the term optical coherence domain reflectometer (OCDR) is used to refer to a system that employs a light source in an optical interferometer to achieve high resolution with a large dynamic range in terms of resolving the light signals reflected or scattered from a sample. Hence the term OCDR covers various modification of the basic technology, which, in addition to the traditional or conventional OCDR/OCT, also includes frequency-domain or Fourier-domain or spectral-domain optical coherence tomography.

An important feature in the presently disclosed configuration of the invention is a combined use of a polarization beam splitter with one or two polarization manipulator(s) that rotate the returned light wave polarization to an orthogonal direction. Such a combination brings a number of advantages to an OCT system, including optimized interference fringe visibility and hence enhanced SNR with shot noise limited interference detection, fixed or predetermined polarization state of the output interfering light waves, insensitivity to fiber birefringence fluctuations, dispersion matching and others as will be made clear below.

Embodiment 1

FIG. 6A is a diagram of the OCDR system according to a first embodiment of the present invention. The light source 610a introduces to the system 600a a linearly polarized light wave either through a linearly polarized light source 610a or by placing a linear polarizer (not shown) directly after an unpolarized source, wherein the linear polarizer can be an independent polarizer or the polarizing beam splitter as will be made clear below. The light source 610a has a center wavelength within the optical spectrum range from ultra-through violet to near infrared. It is preferably derived from a superluminescent diode (SLD), a light emitting diode (LED), a short pulsed laser such as a Ti:sapphire laser, a photonic crystal fiber laser or a spontaneous emission based rare earth doped optical fiber broad band light source. For these applications, the latter light sources are considered "low coherence" light sources. The subject invention can also be implemented with a frequency swept laser. The light source 610a is coupled through a short length of a non-PM fiber 612a to the input port (port I) of a polarizing/polarization beam splitter (PBS) 614a. It is well known to those skilled in the art that the PBS 614a may be based on a polarization beam splitter cube, in which case the light wave from a fiber needs to be collimated using, for example, a graded refractive index (GRIN) lens, and refocused into another fiber using, for example, another GRIN lens, if this is desired. The PBS may also be purely fiber optics based in which case polarization-maintaining (PM) fibers may be present. It should also be noted that as the light source 610a can be polarized or unpolarized, if it is polarized, a polarization-maintaining (PM) fiber may have already been pig-tailed for the light source and such a PM fiber can be used to connect the light source 610a to the PBS 614a to maintain the polarization state. It should be pointed out that non-PM fiber or PM fiber pig-tailed polarization beam splitters are commercially available and their price is much less than that of a fiber pig-tailed optical circulator. Preferably, the polarized light wave from the light source arm is already in the correct polarization state or direction so that except for the insertion loss introduced by the polarizing beam splitter 614a, the input light power is substantially coupled to the output port (port II). If the input polarization state is not in the desired state or direction, a non-PM single mode fiber based polarization controller 611a can be placed in front of the PBS 614a to adjust the input polarization state to the desired direction. Although a non-PM fiber based polarization controller 611a is preferred here, other types of polarization controller can also be used, for example, a bulk optical wave plate based polarization controller is also a choice. Meanwhile, in spite of the fact that a non-PM fiber pig-tailed polarizing beam splitter is preferred here, this statement does not exclude the use of PM fiber pig-tailed PBS, although the latter may be more expensive than the former due to the additional requirement of rotational alignment of the PM fibers.

The polarized output from port II of the polarizing beam splitter 614a is sent through a short length of non-PM fiber 616a to a non-polarizing beam splitter or a non-PM fiber based coupler 618a having a desired optical power split ratio $$\frac{\alpha}{1-\alpha}$$

(say, for example, $$\frac{\alpha}{1-\alpha} = \frac{90}{10})$$

so that most of the light (for example α=at least 70% and preferably 90%) is coupled to the sample arm 620a and a small portion of the input light (for example (1−α)=10%) is coupled to the reference arm 622a.

The sample arm contains a certain length of a non-PM single mode fiber 624a, an optical probe module 630a and a sample 632a. The non-PM single mode fiber 624a can have any reasonable length as long as it approximately matches the length and dispersion property of the non-PM single mode fiber 640a in the reference arm 622a. It should be noted that here dispersion matching is desirable but not absolutely required. A preferred practice is to cut a single piece of a non-PM fiber into two pieces of substantially the same length with one for the sample arm and the other for the reference arm so that their dispersion property is also well matched.

The optical probe module 630a includes some light beam shaping and focusing elements, light beam bending or steering or scanning elements (not shown) such as pivoted scanning or dithering mirrors, and a polarization manipulator 634a, wherein the polarization manipulator can be a Faraday rotator or a wave plate. It should be noted that in the optical probe module 630a, the arrangement of various optical elements can be of any order or sequence. Although it is preferred that the polarization manipulator 634a is placed at the end of the sample arm just in front of the sample, in practice, it may be more reasonable to place the polarization manipulator 634a before any translational or mechanically movable components, and perhaps the easiest place to put it is at the end or tip of the fiber 624a, as such a Faraday rotator tipped fiber piece is commercially available.

Figure 4:
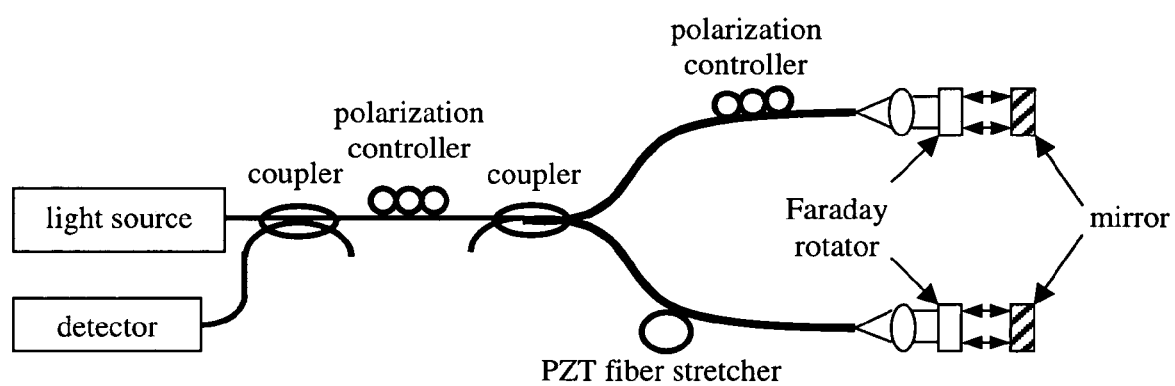
FIG. 4 shows a prior art polarization insensitive Michelson interferometer configuration in which two 45° Faraday rotators are used at the end of the sample and reference arms.
Figure 5:
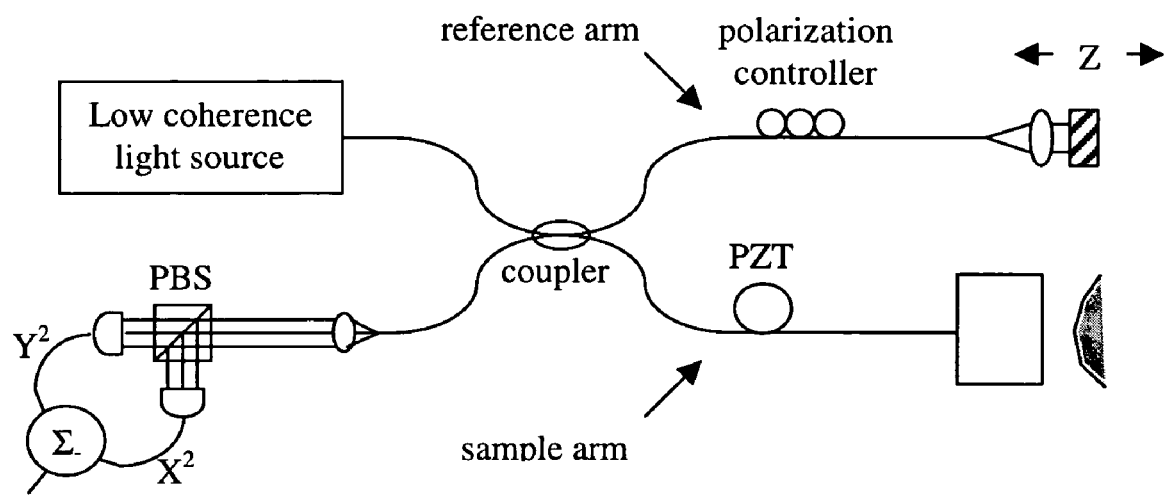
FIG. 5 shows another prior art polarization insensitive configuration called polarization diversity detection scheme.

Light reflected from various optical interfaces or scattered from within the sample 632a is collected by the same optical probe module 630a and is directed back through the same non-PM optical fiber 624a in the sample arm 620a to the non-polarizing beam splitter or the non-PM fiber coupler 618a. Note that if the polarization manipulator is a 45° Faraday rotator 634a as discussed previously with respect to FIG. 4 and the sample, when reflecting or scattering the light wave, does not alter the light wave polarization direction, the polarization state or direction of the returned light wave will be rotated by 90° after double-passing the non-reciprocal Faraday rotator 634a to an orthogonal direction with respect to the polarization direction of the original forward-propagating light beam before it hits the Faraday rotator 634a. Thus, except for the biological sample or components in the sample arm after the Faraday rotator 634a, any birefringence-induced polarization sensitivity or fading effect introduced to the sample arm light wave in the forward direction will be completely compensated for or cancelled when the light wave propagates in the backward direction. It should be highlighted that because of this feature, if a polarization controller is included in the fiber section 624a of the sample arm 620a, a desired final polarization state of the light beam shining onto the sample can be selected to take full advantage of a biological sample if its light reflection or scattering property is polarization dependent and this polarization controlling will obviously not influence the final well-aligned interfering beam polarization directions from the sample arm and the reference arm (as will be discussed shortly) because of the polarization-insensitive fiber optic Michelson interferometer configuration. For example, one can maximize the final optical interference signal if for certain optical boundaries or interfaces the amount of reflected light is more intense in one polarization direction than the other or to examine the birefringence properties of the biological sample.

On the other hand, if the sample is a biological sample that has a relatively large birefringence that can not be ignored and is more or less predictable, the polarization manipulator may be selected in such a way that when it is combined with the birefringence of the biological sample, a substantially 90° polarization direction rotation for the returned light wave with respect to the original forward propagating light wave is realized. Such a polarization manipulator can be either a wave plate or a combination of a polarization controller and a wave plate, wherein the polarization controller can select a desired polarization direction with respect to the wave plate and the biological sample, and the wave plate can combine its birefringence with that of the biological sample to provide a net quarter wave plate effect.

Figure 2:
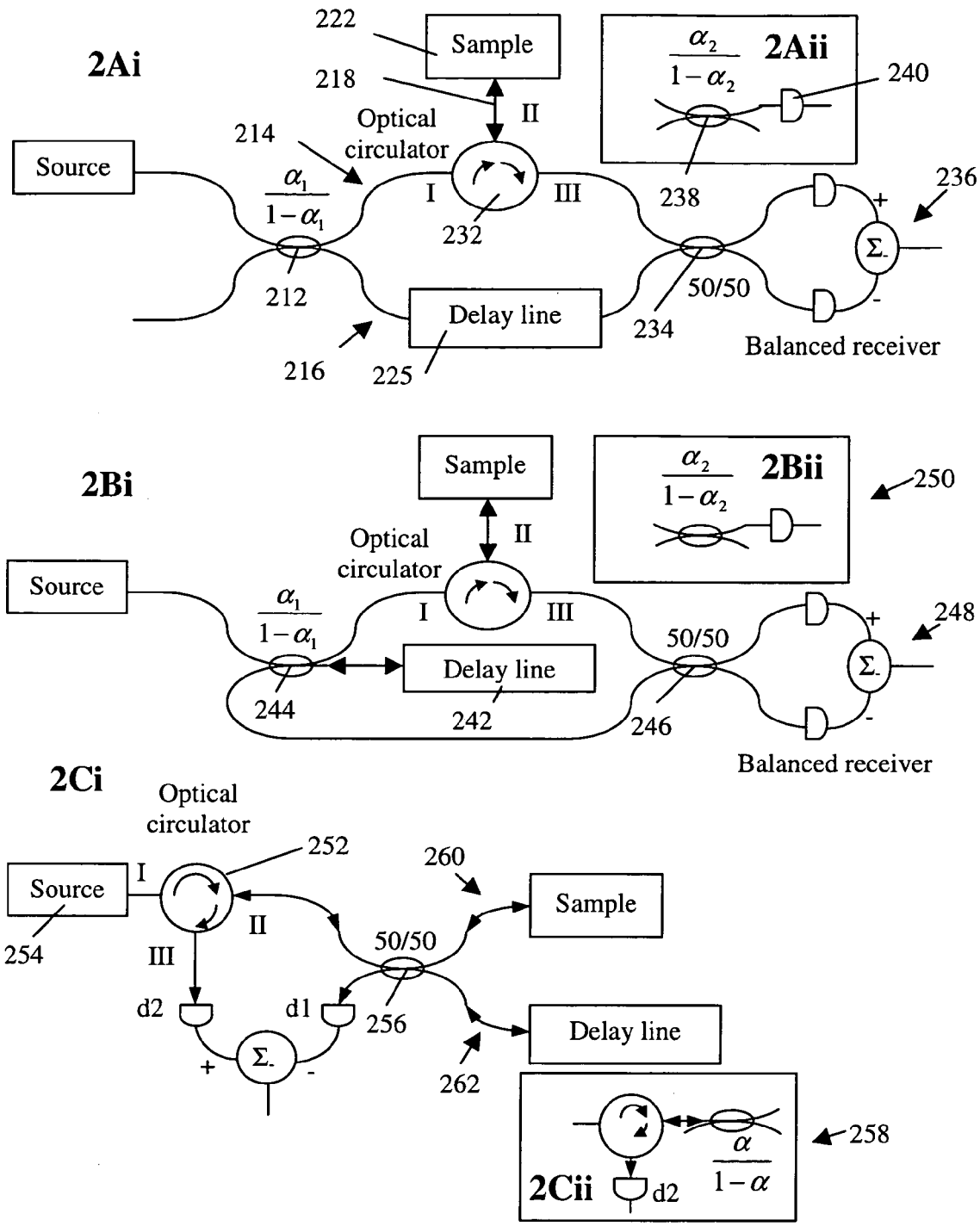
FIG. 2 shows 6 different interferometer configurations in which the optical power delivery efficiency to the detector(s) is improved as compared to the standard Michelson interferometer configuration.
Figure 3:
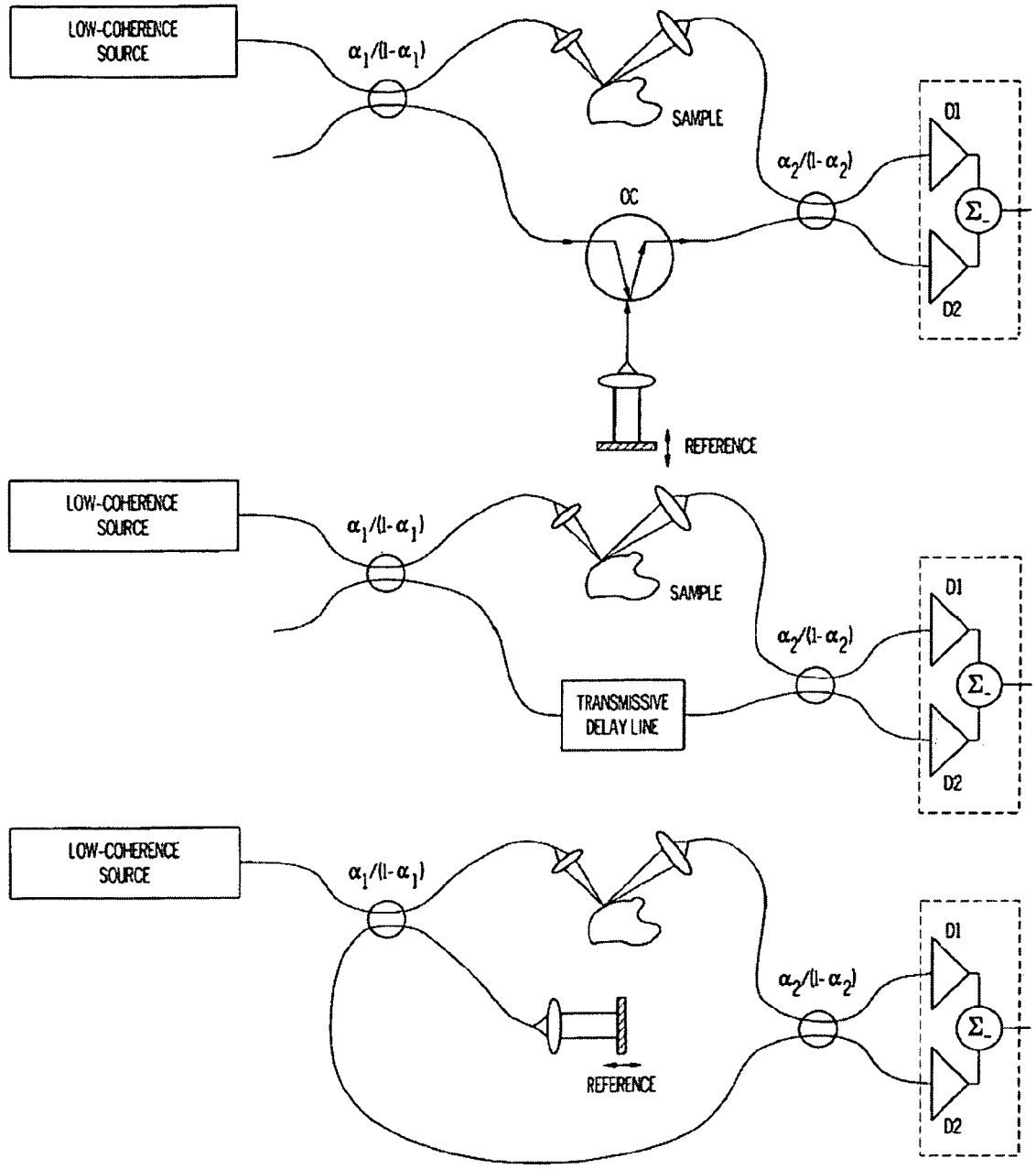
FIG. 3 shows some extensions of FIG. 2 in which the sample arm is transmissive in the sense that the illumination and collection optics geometry occupy separate optical paths

When the returned light wave from the sample arm 620a passes though the non-polarizing beam splitter or the non-PM fiber coupler 618a back to the non-PM fiber 616a, the optical power will be further attenuated by a factor of α (for example, α=90%) as has been discussed previously with respect to FIG. 2Cii. As a result, the overall attenuation to the sample light wave introduced solely by the non-polarizing beam splitter or the non-PM fiber coupler 618a for a round trip will lead to an optical power efficiency of $\alpha^2$ (for example: $\alpha^2$=90%×90%=81%). It is assumed here that the optical power split ratio of the non-polarizing beam splitter or the non-PM fiber based coupler 618a is polarization-independent, which is generally the case. However, the statement should not exclude the case of a non-PM fiber based coupler that may be slightly polarization sensitive due to imperfection in the fabrication of the coupler and in which case, the attenuation for the returned light wave may be slightly different from that for the forwarding propagating light wave.

Note that as the polarization direction is now rotated by 90° for the returned light wave from the sample arm 620a to the polarizing beam splitter 614a, except for the insertion loss, basically all of the returned light wave will now be channeled to port III of the polarizing beam splitter 614a (as is well known to those skilled in the art), and if both the non-polarizing beam splitter or the non-PM fiber coupler 618a and the polarizing beam splitter 614a are perfect, there will be no light returning to the light source arm. This is obviously an advantage as has already been discussed with reference to FIG. 2 because any returned light to the light source might disturb the light emitting property.

Furthermore, if a short length of non-PM fiber 650a is used to guide the light wave to a detector (or a light detection module) 652a such that the polarization state is not altered by the short length of the non-PM fiber 650a, the polarization state (or direction) of the light wave reaching the detector (or light detection module) 652a will be fixed and predetermined. While for a polarization independent photodetector, this fixed and predetermined polarization state of the arriving light wave is not critical, it is actually very critical for the spectral-domain optical coherence tomography (SD-OCT) detection scheme since in such a system, the grating used to disperse the constituent wavelength components of the broadband optical signal is generally sensitive to the polarization direction of the input beam and hence a fixed or predetermined polarization direction of the input beam to the grating will be extremely beneficial.

In the reference arm, there should preferably be a non-PM single mode fiber 640a that is approximately matched in length and dispersion property with the non-PM single mode fiber 624a in the sample arm. It is preferred that the optical delay line 642a is incorporated in the reference arm 622a and this reference delay line 642a may be a transmissive one to be implemented in the fiber section 622a which can be achieved by wrapping a certain length of optical fiber around a piezoelectric cylinder. In fact, for a standard polarization sensitive OCT configuration such as those shown in FIG. 1 and FIG. 2, such an optical fiber wrapped PZT based optical delay line will generally introduce a substantial amount of polarization fading as a result of the birefringence change during the optical path length scanning or optical phase modulation process, but with the presently invented configuration, this is no longer an issue any more because of the polarization insensitivity nature and hence it might be advantageous to use such a fiber wrapped PZT based optical path length delay line. Although implementing the optical delay line in the reference arm 622a is preferred here, it should be noted that the optical delay line can also be located in the sample arm or both arms may have an optical delay line with the two operating in a push-and-pull mode or in any other manners as desired such as with one modulating the path length to achieve a depth scan and the other modulating the optical phase to obtain a high carrier frequency for the interference signal. Alternatively, an independent optical delay line may be used after the fiber 640a and a good example is a grating based phase control optical delay line as disclosed in U.S. Pat. Nos. 6,111,645 and 6,282,011. Other retro-reflective optical delay lines such as those employing corner mirror(s) or corner prism cube(s) may also be used. The overall optical path length for the reference arm 622a should roughly match that of the sample arm 620a and this can be achieved by letting the reference light wave traveling through some free space and/or some other optical elements. By roughly matching the overall optical path length between the reference arm 622a and the sample arm 620a, the requirement for the scan range of the optical delay line 642a can be lowered and data acquisition time for one depth scan can thus be reduced to a minimum. The reference arm 622a may also contain some light collimating and/or focusing optical elements 644a, and there should be a polarization manipulator such as a 45° Faraday rotator 646a and a mirror 648a to reflect the reference light wave back to the non-polarizing beam splitter or the non-PM fiber coupler 618a. The position of the 45° Faraday rotator 646a is preferably at the end of the reference arm 622a and right in front of the mirror 648a so that polarization fading caused by any birefringence or birefringence fluctuations introduced by all the optical elements prior to the Faraday rotator 646a in the reference arm 622a can be completely compensated for and hence cancelled. However, it should be noted that the 45° Faraday rotator 646a can be placed anywhere between the end of the non-PM fiber 640a and the mirror 648a. It is perhaps more economic to directly use a mirrored 45° Faraday rotator as such a device is now commercially available, and in such a case, the reference arm fiber 640a may be selected to be longer than the sample arm fiber 624a such that the overall optical path length between the sample arm 624a and the reference arm 622a is roughly matched.

Similar to what has been discussed for the sample arm 620a, the light wave returned from the mirror 648a is collected by the same optical element(s) 644a & 646a and is directed back through the same non-PM optical fiber 640a in the reference arm 622a to the non-polarizing beam splitter or the non-PM fiber coupler 618a. Due to the use of the 45° Faraday rotator 646a, the polarization state or direction of the returned light wave will be rotated by 90° after double-passing the non-reciprocal Faraday rotator 646a to an orthogonal direction with respect to the polarization direction of the original forward-propagating light wave in the reference arm 622a before it hits the Faraday rotator. As a result, any birefringence-induced polarization sensitivity or fading effect introduced to the reference arm light wave in the forward direction will be completely compensated for or cancelled when the light wave propagates in the backward direction.

When the returned light wave from the reference arm 622a passes through the non-polarizing beam splitter or the non-PM fiber coupler 618a back to the non-PM fiber 616a, the optical power of the reference wave will be further attenuated by a factor of $1-\alpha$ (for example, $1-\alpha=10\%$). Note that the overall attenuation to the reference light wave introduced solely by the non-PM fiber coupler 618a for a round trip will have an optical power efficiency of $(1-\alpha)^2$ (for example: $(1-\alpha)^2=10\%\times10\%=1\%$), which is different from that to the sample arm ($\alpha^2$, for example: $\alpha^2=90\%\times 90\%=81\%$). For OCT based bio-sample imaging, a low optical power efficiency for the reference arm 622a is desirable as long as the photon shot noise from the reference arm 622a is above the detector circuit noise. Ideally, one would select a non-polarizing beam splitter or a fiber coupler 618a that couples as much light as possible to the sample arm 620a, while leaving enough light from the reference arm 622a to maintain the shot noise just above detector circuit noise.

Similar to the case of the sample arm 620a, as the polarization direction is now rotated by 90° for the returned light wave from the reference arm 622a to the polarizing beam splitter 614a, except for the insertion loss, basically all of the returned light wave will now be channeled to port III of the polarizing beam splitter 614a, assuming that the mirror 648a in the reference arm 622a preserves the light wave polarization state, if the non-polarizing beam splitter or the non-PM fiber coupler 618a and the polarizing beam splitter 614a are perfect, there will be no light returned to the light source 610a and the polarization directions of the reference-arm-returned-light wave and the sample-arm-returned-light wave will be the same. If a short length of a non-PM fiber 650a is used to guide the returned interfering light waves to a detector (or a light detection module) 652a such that the polarization state is not altered by the short length of the non-PM fiber 650a, the polarization state or direction of the returned light waves reaching the detector (or light detection module) 652*a* will be fixed and predetermined. As has already been pointed out; this is especially beneficial to spectral domain optical coherence tomography (SD-OCT). It should also be mentioned that the use of the non-PM fiber 650*a* is not absolutely necessary, in fact, the detector or light detection module 652*a* may be directly placed or bonded next to the PBS 614*a* and in such a case, the requirement to focus the returned interfered light beam into a single mode fiber may be eliminated as a photodetector generally has a relative large light sensitive area and this may save cost for the systems.

It should be noted that while in FIG. 6A, a fiber optics version of the first embodiment of the present invention is illustrated; a bulk optics based free space version is obviously a natural extension of the invention. It should be pointed out that in certain cases, the bulk optics version may provide other advantages. For example, with bulk optics, the two 45° Faraday rotators may be replaced by two quarter wave plates which may be less expensive, and the need to expand and collimate a light beam from a single mode fiber, and to refocus the expanded beam back into another single mode optical fiber, may be eliminated, which may also save cost for the system.

FIG. 6B shows a bulk optics version of the first embodiment of the present invention. As the bulk optics version is very similar to the fiber optics version, the description below will only mainly highlight the differences rather than repeating the details. The light source 610*b* can be either a fiber pigtailed or non-fiber-pigtailed but collimated light source. If it is fiber pig-tailed, a collimating lens needs to be used to collimate the output beam. As in the fiber optics version case, the light source can be either originally linearly polarized or externally linearly polarized by placing a linear polarizer (not shown) directly after an unpolarized source or by using the polarizing beam splitter 614*b* to polarize it. The light source 610*b* is directed through a free space 612*b* to the input port (port I) of a polarizing/polarization beam splitter (PBS) cube 614*b*. It is desirable that the input linearly polarized light wave is already in the correct polarization state or direction and hence the optical power is substantially transmitted to the output port (port II).

The light wave from port II of the polarizing beam splitter 614*b* is directed through a free space 616*b* to a non-polarizing beam splitter (NPBS) 618*b* with a desired optical power split ratio of $$\frac{\alpha}{1-\alpha},$$

such that most of the light is coupled to the sample arm 620*b* and a small portion of the input light is coupled to the reference arm 622*b*.

The light wave in the sample arm travels through a free space optical path 624*b* to an optical probe module 630*b*, in which the light beam is scanned and focused onto a sample 632*b*. A polarization manipulator such as a quarter wave plate or a 45° Faraday rotator 634*b* is placed in the probe module 630*b* to enable the polarization rotation of the returned light wave by 90°. Note that when a quarter wave plate is used, although it may be cheaper than a 45° Faraday rotator, the projected light wave onto the sample will be circularly polarized instead of linearly polarized as in the case of a 45° Faraday rotator. Hence the use of a quarter wave plate will not deliver a linearly polarized light wave to the sample 632*b* as in the case of a 45° Faraday rotator, where a free space based polarization controller may be inserted in the sample arm path 624*b* to deliver a desired polarization direction to the sample 632*b* as in the fiber optics version case.

The returned light wave from the sample 632*b* is collected by the probe module 630*b*, directed back to the NPBS 618*b*, where it is further split with a larger optical power splitting percentage of a back towards the PBS 614*b*.

Similarly, for the reference arm, the use of a quarter wave plate or a 45° Faraday rotator 646*b* will rotate the polarization direction of the returned light wave by 90°. Note that since the mirror 648*b* does not need a preferred polarization state and there is generally no birefringence change for a light wave traveling in free space, a quarter wave plate can always be used anywhere in the reference arm, although a more expensive 45° Faraday rotator can also be used. In addition to an approximate optical path length matching between the sample arm and the reference arm, a dispersion matching optical element can also be used in the reference arm. Similar to the fiber optics version case, the optical delay line 642*b* is preferably incorporated in the reference arm 622*b*.

The light wave returned from the reference mirror 648*b* is directed back through the same free space optical path 640*b* to the non-polarizing beam splitter NPBS 618*b* and is split with a smaller optical power percentage of (1−α) towards the polarizing beam splitter PBS 614*b*.

Note that since the polarization direction of the returned light waves from both the sample arm and the reference arm have been rotated by 90° with respect to the original forward traveling light wave, basically all of the two returned light waves will now be channeled to port III of the polarizing beam splitter 614*b*. Obviously, the polarization state or direction of the returned light waves reaching the detector (or light detection module) 652*b* will be fixed and predetermined. A detector or a detection module 652*b* can be used to collect the two interfering light waves to convert the interfered optical power into an electrical signal for further processing.

Note that the optical path 650*b* can be a free space path and can be shortened to a minimum by placing the detector or detection module 652*b* next to the PBS 614*b*. Alternatively, a fiber pig-tailed detector or detection module may be used and in such a case the optical path 650*b* may represent a short length of optic fiber and wherein there will be a need to focus the free space light beam into such an optical fiber.

As a further extension to FIG. 6A and FIG. 6B, FIG. 6C shows another free space optics version of an implementation of embodiment 1. Instead of using two polarization manipulators as in FIG. 6A and FIG. 6B, FIG. 6C uses only one polarization manipulator 670*c* in the common optical path portion between the PBS 614*c* and the NPBS 618*c* to rotate the polarization of the two returned light waves from the sample arm and the reference arm respectively to an orthogonal direction. Similar to the argument of FIG. 6B, as the retuned light waves to the PBS 614*c* have an orthogonal polarization, they will be completely channeled to port III and hence to the detector 652*c* with a fixed or predetermined polarization direction.

It should be noted that the polarization manipulator 670*c* can be either a quarter wave plate or a 45° Faraday rotator. A quarter wave plate is preferred here due to its lower price and in such a case, the light wave to the right side of the quarter wave plate will be circularly polarized and will be further split by the NPBS 618*c* into the sample arm and the reference arm with a desired optical power split ratio. On the other hand, if a 45° Faraday rotator is used, the light wave to the right side of the Faraday rotator will be linearly polarized but with an azimuth orientation that is 45° with respect to the incident light wave on the left side of the 45° Faraday rotator. Such a linearly polarized light wave will be further split into the sample arm and the reference arm by the NPBS 618c with a desired optical power split ratio. Note that in the latter case, a free space based polarization controller may be inserted in the sample arm path 624c to deliver a desired polarization direction to the sample 632c as in the fiber optics version case.

Upon reflection from the biological sample and the reference mirror, the returned light waves will be further split by the NPBS 618c toward the polarization manipulator 670c. Due to the fact that the light wave propagating toward the PBS 614c from the sample arm will have transmitted through the NPBS 618c twice, whereas the light wave propagating toward the PBS 614c from the reference arm will have been reflected twice by NPBS 618c, the optical power delivery efficiency can hence be made very high by splitting most of the optical power to the sample arm.

It should be understood that the rest of the embodiment of FIG. 6C is similar to what has been discussed for FIG. 6A and FIG. 6B and hence will not be repeated here. Note that the embodiment of FIG. 6C may be especially advantageous for free space based SD-OCT system such as SD-OCT microscopes as the cost is even lower than that of FIG. 6B. It should also be understood that a combination of various features of FIG. 6A, FIG. 6B and FIG. 6C can be selected to suit various applications. For example, one may select a fiber based sample arm for easy and flexible light delivery to a biological sample together with a 45° Faraday rotator to render the sample arm insensitive to birefringence fluctuations and, to save costs, the reference arm can be a free-space optics based configuration with a quarter wave plate.

Embodiment 2

FIG. 7A is a diagram of the OCDR system according to a second embodiment of the present invention. The light source 710a introduces to the system 700a a linear polarized light wave either through a linearly polarized light source 710a or by placing a linear polarizer (not shown) directly after an unpolarized source. The light source 710a has a center wavelength within the optical spectrum range from ultra-violet to near infrared. It is preferably derived from a superluminescent diode (SLD), a light emitting diode (LED), a frequency swept laser, a short pulsed laser such as a Ti:sapphire laser, a photonic crystal fiber laser or a spontaneous emission based rare earth doped optical fiber broad band light source. The light source 710a is coupled through a short length of a non-PM fiber 712a to the input port (port I) of a polarizing/polarization beam splitter (PBS) 714a. Assuming that the PBS has two polarization modes or directions that are in the vertical and horizontal directions respectively, compared to embodiment 1, the polarization direction of the input light wave of embodiment 2 is neither in the vertical nor in the horizontal direction but is rather selected to lie in a direction in between these two axis. As a result of this selection, assuming that there is no loss of optical power at the PBS, a certain percentage of the input optical power (for example $\alpha_1$=90%) will be channeled port II of the PBS 714a and hence to the sample arm 720a and the remaining input optical power (for example (1–$\alpha$)=10%) will then be channeled to port III of the PBS 714a and hence to reference arm 722a. It is well known to those skilled in the art that the polarization directions of the two light waves in the sample and reference arms are orthogonal or perpendicular with respect to each other. Note that the PBS 714a may be based on a polarization beam splitter cube, in which case the light wave from a fiber needs to be collimated using, for example, a graded refractive index (GRIN) lens and refocused into another fiber using, for example, another GRIN lens, if this is desired. The PBS 714a may also be purely fiber optics based in which case polarization-maintaining (PM) fibers may be present. It should also be noted that as the light source 710a can be polarized or unpolarized, if it is polarized, a polarization-maintaining (PM) fiber may have already been pig-tailed for the light source and such a PM fiber can be used to connect the light source 710a to the PBS 714a to maintain the polarization state. It should be pointed out that non-PM fiber or PM fiber pig-tailed polarization beam splitters are commercially available and their price is much less than that of a fiber pig-tailed optical circulator. Hence such fiber pigtailed PBS may be used directly. Preferably, the polarized light wave from the light source arm is already in the desired polarization state or direction to enable a desired percentage of the input optical power to the sample and reference arms respectively. Note that compared to embodiment 1 of FIG. 6A, the PBS 714a of FIG. 7A also serves the purpose of the fiber coupler 618a of FIG. 6A, i.e. to split the input optical power at a desired ratio into the sample and reference arms. If the input polarization state is not in the desired direction, a non-PM single mode fiber based polarization controller 711a can be placed in front of the PBS 714a to adjust the input polarization state to the desired direction. Although a non-PM fiber based polarization controller 711a is preferred here, other types of polarization controller can also be used, for example, a bulk optical wave plate based polarization controller is also a choice. Meanwhile, in spite of the fact that a non-PM fiber pig-tailed polarizing beam splitter (PBS) is preferred here, this statement does not exclude the use of PM fiber pig-tailed PBS, although the latter may be more expensive than the former due to the additional requirement of rotational alignment of the PM fibers.

The polarized output from port II of the polarizing beam splitter 714a is sent through a non-PM single mode fiber 724a and an optical probe module 730a to a sample 732a. The non-PM single mode fiber 724a can have any reasonable length as long as it approximately matches the length and dispersion property of the non-PM single mode fiber 740a in the reference arm 722a. It should be noted that here dispersion matching is desirable but not absolutely required. A preferred practice is to cut a single piece of a non-PM fiber into two pieces of substantially the same length with one for the sample arm and the other for the reference arm so that their dispersion property is also well matched.

The optical probe module 730a includes some light beam shaping and focusing elements, light beam bending or steering or scanning elements (not shown) such as pivoted scanning or dithering mirrors, and a polarization manipulator such as a 45° Faraday rotator or a quarter wave plate 734a. It should be noted that in the optical probe module 730a, the arrangement of various optical elements can be of any order or sequence. Although it is preferred that a Faraday rotator 734a is placed at the end of the sample arm just in front of the sample, in practice, it may be more reasonable to place the Faraday rotator 734a before any translational or mechanically movable components, and perhaps the easiest place to put it is at the end or tip of the fiber 724a as such a Faraday rotator tipped fiber piece is commercially available.

Light reflected from various optical interfaces or scattered from within the sample 732a is collected by the same optical probe module 730a and is directed back through the same non-PM optical fiber 724a in the sample arm 720a to the PBS 714a. Note that due to the use of the 45° Faraday rotator 734a as discussed previously with reference to FIG. 4, the polarization state or direction of the returned light wave will be rotated by 90° after double-passing the non-reciprocal Faraday rotator 734a to an orthogonal direction with respect to the polarization direction of the original forward-propagating light wave before it hits the Faraday rotator 734a. Thus, except for the sample or components in the sample arm after the Faraday rotator 734a, any birefringence-induced polarization sensitivity or fading effect introduced to the sample arm light wave in the forward direction will be completely compensated for or cancelled when the light wave propagates in the backward direction. It should be highlighted that because of this feature, if a polarization controller is included in the fiber section 724a of the sample arm 720a, a desired final polarization state of the light beam shining onto the sample can be selected to take full advantage of a biological sample if its light reflection or scattering property is polarization dependent and this polarization controlling will obviously not influence the final polarization direction of the returned light wave from the sample arm. For example, one can maximize the final optical interference signal if, for certain optical boundaries or interfaces, the amount of reflected light is more intense in one polarization direction than the other or to examine the birefringence properties of a biological sample using this approach.

On the other hand, if the sample is a biological sample that has a relatively large birefringence that can not be ignored and is more or less predictable, the polarization manipulator may be selected in such a way that when it is combined with the birefringence of the biological sample, a substantially 90° polarization direction rotation for the returned light wave with respect to the original forward propagating light wave is realized. Such a polarization manipulator can be either a single wave plate or a combination of a polarization controller and a wave plate, wherein the polarization controller can select a desired polarization direction with respect to the wave plate and the biological sample, and the wave plate can combine its birefringence with that of the biological sample to provide a net quarter wave plate effect.

When the returned light wave from the sample arm 720a returns to the PBS 714a, as the polarization direction is now rotated by 90°, except for the insertion loss which can be assumed to be zero for ease of discussion, basically all of the returned light wave will now be channeled to port IV of the polarizing beam splitter 714a (as is well known to those skilled in the art), and if the polarizing beam splitter 714a is perfect, there will be no light returning to the light source 710a. This is obviously an advantage as has already been discussed with reference to FIG. 2, because any returned light to the light source might disturb the light emitting property.

For the light wave sent through port III of the PBS 714a to the reference arm 722a, the wave will propagate to a polarization manipulator such as a Faraday rotator or a quarter wave plate 746a and a mirror 748a through a non-PM single mode fiber 740a that is approximately matched in length and dispersion property with the non-PM single mode fiber 724a in the sample arm 720a. It is preferred that the optical delay line 742a for depth scanning is incorporated in the reference arm 722a. This reference delay line 742a may be a transmissive one to be implemented in the fiber section 722a, which can be achieved by wrapping a certain length of optical fiber around a piezo-electric stretcher. In fact, for a standard polarization sensitive OCT configuration such as those shown in FIG. 1 and FIG. 2, such an optical fiber wrapped PZT based optical delay line will generally introduce a substantial amount of polarization fading as a result of the birefringence change during the optical path length scanning or optical phase modulation process, but with the presently invented configuration, this is no longer an issue because of the polarization insensitivity nature and hence it might be advantageous to use such a fiber wrapped PZT based optical path length delay line. Although implementing the optical delay line in the reference arm 722a is preferred here, it should be noted that the optical delay line can also be located in the sample arm or both arms may have an optical delay line with the two operating in a push-and-pull mode or in any other manners as desired such as with one modulating the path length to achieve a depth scan and the other modulating the optical phase to obtain a high carrier frequency for the interference signal. Alternatively, an independent optical delay line may be used after the fiber 740a and a good example is a grating based phase control optical delay line as disclosed in U.S. Pat. Nos. 6,111,645 and 6,282,011. Other retro-reflective optical delay lines such as those employing corner mirror(s) or corner prism cube(s) may also be used. The overall optical path length for the reference arm 722a should roughly match that of the sample arm 720a and this can be achieved by letting the reference light wave traveling through some free space and/or some other optical elements. By roughly matching the overall optical path length between the reference arm 722a and the sample arm 720a, the requirement for the scan range of the optical delay line 742a can be lowered and data acquisition time for one depth scan can thus be reduced to a minimum. The reference arm 722a may also contain some light beam shaping and/or focusing optical elements 744a in addition to the polarization manipulator such as a 45° Faraday rotator 746a and the mirror 748a. The position of the 45° Faraday rotator 746a is preferably at the end of the reference arm 722a and right in front of the mirror 748a so that polarization fading caused by any birefringence or birefringence fluctuations introduced by all the optical elements prior to the Faraday rotator 746a in the reference arm 722a can be completely compensated for and hence cancelled. However, it should be noted that the 45° Faraday rotator 746a can be placed anywhere between the end of the non-PM fiber 740a and the mirror 748a. It is perhaps even more economic to directly use a mirrored 45° Faraday rotator with a non-PM fiber pig-tail as such a device is now commercially available, and in such a case, the reference arm fiber 740a may be selected to be longer than the sample arm fiber 724a such that the overall optical path length between the sample arm 720a and the reference arm 722a is roughly matched.

Similar to what has been discussed for the sample arm 720a, the light wave returned from the mirror 748a is collected by the same optical element(s) 744a & 746a and is directed back through the same non-PM optical fiber 740a in the reference arm 722a to the PBS 714a. Due to the use of the polarization manipulator such as a 45° Faraday rotator 746a, the polarization state or direction of the returned light wave will be rotated by 90° after double-passing the non-reciprocal Faraday rotator 746a to an orthogonal direction with respect to the polarization direction of the original forward-propagating light wave in the reference arm 722a before it hits the Faraday rotator 746a. As a result, any birefringence-induced polarization sensitivity or fading effect introduced to the reference arm light wave in the forward direction will be completely compensated for or cancelled when the light wave propagates in the backward direction.

When the returned light wave from the reference arm 722a arrives at the PBS 714a, its polarization direction is now rotated by 90°, except for the insertion loss which is assumed zero for the ease of discussion, basically all of the returned light wave will now be channeled to port IV of the polarizing beam splitter 714a, assuming that the mirror 748a in the reference arm 722a preserves the light wave polarization state, if the polarizing beam splitter 714a is perfect, there will be no light returned to the light source 710a. Compared to embodiment 1, a major difference here is that the polarization directions of the reference-arm-returned-light wave and the sample-arm-returned-light wave are orthogonal or perpendicular to each other. As a result, if one directly puts a detector to detect these two waves, there will be no interference signals as is well known to those skilled in the art.

To extract the interference signal, one needs to project the two orthogonally polarized light waves onto a common polarization-passing-through-direction and there are two possible approaches. The first one is to arrange another polarizing/polarization beam splitter 752a in such a way that its azimuth orientation is substantially at 45° with respect to that of the first polarizing beam splitter 714a. As is well known to those skilled in the art, by doing so, a balanced heterodyne detection scheme can be realized as shown in FIG. 7A. To save cost, the second polarizing beam splitter 752a can actually be glued or bonded to the first polarizing beam splitter 714a so that they become a rigid solid module together with the two detectors D1 and D2.

However, the above statements should not exclude the use of a short length of a non-PM fiber 750a between the first PBS 714a and the second PBS 752a, as long as the polarization state is not altered by the short length of the non-PM fiber 750a. The statements also should not exclude the use of a PM fiber between the first PBS 714a and the second PBS 752a, and the reason for this is that a PM fiber pig-tailed PBS with four ports are commercially available and hence can be readily used.

The second approach to extract the interference signal from two orthogonally polarized optical light waves is to use a simple analyzer together with only one detector. As an example, the second polarizing beam splitter can be azimuthally oriented in such a way that an enhanced interference fringe visibility is achieved together with shot noise limited detection as has been discussed before. For example, the orientation direction of the second PBS 752a can be chosen such that while a smaller amount of the optical wave from the reference arm is projected to the polarization-passing-through-axis of the analyzer and a lager amount of the optical wave from the sample arm is projected to the same polarization-passing-through-axis of the analyzer, the amount of optical power from the reference wave also gives a photon shot noise from the reference arm that is just above the detector thermal noise. In fact, in term of optical power delivery efficiency, the second PBS 752a now acts as an unbalanced beam combiner with a non-50/50 power split ratio $$\frac{\alpha_2}{1-\alpha_2},$$

and the optical delivery efficiency is similar to that of FIG. 2Aii, but the present invention is Michelson interferometer based and it makes the system insensitive to polarization fading. It should be pointed out that there is no absolute need to use a cube based second polarizing beam splitter 752a as an analyzer and in fact, it is much cheaper to use a thin film based analyzer that has only one polarization-passing-through-axis and it is even more economical to glue or bond such a thin film based analyzer 754a to the first PBS 714a, as long as the polarization-passing-through-axis is properly oriented (See insert to FIG. 7A). In fact, it might be even more economical to fix or bond a detector (e.g. D1) and the thin film analyzer 754a to the first PBS 714a and in such a case, the requirement to focus the returned light waves into a single mode fiber can be eliminated as a photodetector generally has a relative large light sensitive area and this may save cost for the systems.

Note, however, that these statements should not exclude the possibility of having a PM or non-PM fiber in between the first PBS 714a and the second analyzer. Also they should not exclude the form of the analyzer which can be either a PBS or a film based analyzer or even a fiber version of an analyzer such as a piece of a polarizing fiber.

With the use of the analyzer, the polarization state or direction of the returned light waves reaching the detector (or light detection module) D1 will be fixed and predetermined. As has already been pointed out, this is especially beneficial to spectral domain optical coherence tomography (SD-OCT), also referred to in the literature as frequency or Fourier domain optical coherence tomography, since in such a system, the grating used to disperse the constituent wavelength components of the broadband optical signal is generally sensitive to the polarization direction of the input beam and hence a fixed or predetermined polarization direction of the input beam to the grating will be extremely beneficial.

It should be noted that while in FIG. 7A, a fiber optics version of the second embodiment of the present invention is illustrated, a corresponding bulk optics based free space version could also be implemented. As pointed out already, in certain cases, the bulk optics version may provide other advantages. For example, with bulk optics, the two 45° Faraday rotators, may be replaced by two quarter wave plates, and the need to expand and collimate a light beam from a single mode fiber, and to refocus the expanded/collimated beam back into another single mode optical fiber, may be eliminated, which may save cost for the system.

FIG. 7B shows a bulk optics version of the second embodiment of the present invention. In order not to repeat all the details again, the description below will only highlight the main differences. The light source 710b is preferably a non-fiber-pigtailed, collimated light source such as one with a TO can package, but can be fiber pig-tailed, in which case a collimating lens needs to be used to collimate the output beam. As in the fiber optics version case, the light source can be either originally linearly polarized or externally linearly polarized by placing a linear polarizer 713b directly after an unpolarized source. The light source 710b is directed through a free space 712b to the input port (port I) of a polarizing/polarization beam splitter (PBS) cube 714b. It is assumed that the input linearly polarized light wave is already in a desired polarization state or direction such that a large portion of input optical power is split into the sample arm 720b via port II of the PBS cube 714b and a small portion of the input optical power is split into the reference arm 722b via port III of the PBS cube 714b.

The light wave in the sample arm travels through a free space optical path 724b to an optical probe module 730b, in which the light beam is scanned and focused onto a sample 732b. A quarter wave plate or a 45° Faraday rotator 734b is placed in the probe module 730b to enable the polarization rotation of the returned light wave by 90°. Note that when a quarter wave plate is used, although it may be cheaper than a 45° Faraday rotator, the projected light wave onto the sample 732b will be circularly polarized instead of linearly polarized as in the case of a 45° Faraday rotator. Hence the use of a quarter wave plate will not deliver a linearly polarized light wave to the sample 732b as in the case of a 45° Faraday rotator where a free space based polarization controller may be inserted in the sample arm path 720b to deliver a desired polarization direction to the sample 732b as in the fiber optics version case.

Assuming that when reflecting the incident light wave, the biological sample preserves the polarization state, then the returned light wave from the sample 732b, after being collected by the probe module 730b, and directed back to the PBS 714b, will have its polarization direction rotated by 90° with respect to the original forward propagating beam. As is well known to those skilled in the art, the returned sample wave will now be totally directed to port IV of the PBS 714b.

Similarly, for the reference arm, the use of a quarter wave plate or a 45° Faraday rotator 746b will rotate the polarization direction of the returned reference light wave by 90°. Since the mirror 748b does not need a preferred polarization state and there is generally no birefringence change for a light wave traveling in free space, a quarter wave plate can always be used anywhere in the reference arm 722b. In addition to an approximate optical path length matching between the sample arm and the reference arm, a dispersion matching optical element can also be used in the reference arm 722b. Similar to the fiber optics version case, the optical delay line 742b is preferably incorporated in the reference arm 722b.

The light wave returned from the reference mirror 748b is directed back through the same free space optical path 740b to the polarizing beam splitter PBS 714b. Now that its polarization direction has been rotated by 90° with respect to the original forward propagating beam, as is well known to those skilled in the art, the returned reference wave will now be totally directed to port IV of the PBS 714b.

As in the fiber optics version case, the two waves exiting port IV of the PBS 714b have orthogonal polarization and in order to extract the interference signal, an analyzer or another PBS needs to be used. While balanced heterodyne detection can be realized using a 45° azimuthally oriented PBS 752b together with two detectors, a less expensive approach is to use a thin film based analyzer 754b with one detector (See insert, FIG. 7B). Obviously, the polarization state or direction of the interfering light waves reaching the detector(s) will be in the polarization-passing-through-direction of the analyzer and hence is fixed and predetermined by the analyzer 754b or the second PBS 752b, which as mentioned before, is beneficial to SD-OCT detection scheme.

Note that the optical path 750b can be a free space path and can be shortened to a minimum by placing the analyzer 754b or the second PBS 752b together with the detector(s) next to the PBS 714b. Alternatively, a fiber pig-tailed detector or detection module may also be used and in such a case there will be a need to focus the free space light beam into such an optical fiber.

As has been discussed for embodiment 1, it should be understood that a combination of various features of FIG. 7A, and FIG. 7B can be selected to suit various applications. For example, one may select a fiber based sample arm for easy and flexible light delivery to a biological sample together with a 45° Faraday rotator to render the sample arm insensitive to birefringence fluctuations and, to save costs, the reference arm can be a free-space optics based configuration with a quarter wave plate.

It should be pointed out that for the two embodiments, although 45° Faraday rotators and quarter wave plates have been mentioned, the embodiments should not exclude the possibility of using other optical elements to achieve the same goal of rotating the polarization direction of the returned wave to an orthogonal direction with respect to the original forward propagating light wave. As is well known to those skilled in the art, there are other thickness for a Faraday rotator and a wave plate that can serve the same purpose and examples include Faraday rotators with rotation angles equal to 45°+M×90°, or wave plate having an overall retardation of $$\frac{\lambda}{4} + M\frac{\lambda}{2},$$

where M is an integer and λ is the central wavelength of the light source. Hence it should be understood that the 45° Faraday rotator or quarter wave plate can be replaced accordingly as long as the final polarization direction of the returned light wave is in the orthogonal direction with respect to the original forward propagating light wave. Furthermore, even if the birefringence property of the light path in either the sample arm or the reference arm may change or fluctuate, as long as such a change can be monitored and compensated dynamically, one could also achieve the same goal of rotating the returned light wave polarization to the orthogonal direction and a good example is a dynamically controllable quarter-wave plate (QWP), such a QWP can be dynamically tuned in response to changes or fluctuations in the either the sample arm or the reference arm to ensure a total returned polarization direction rotation by 90°.

It should be highlighted that the configurations of the present invention (both embodiment 1 and 2) are relatively simple and hence of relatively low cost. Compared with a standard traditional Michelson interferometer based OCDR system, the main difference in terms of optical components used include a polarizing beam splitter and one or two polarization manupulator(s). Considering that a polarization insensitive fiber pig-tailed optical circulator contains a number of more optical elements in addition to the use of a polarizing beam splitter and some Faraday rotators, the configurations of the present invention will hence cost less than a configuration that include a polarization insensitive fiber pig-tailed optical circulator. By reviewing the prior art configurations, it can be seen that for many of these configurations, their cost will be even higher due to the use of polarization maintaining fibers, the use of additional 22.5° Faraday rotators and other additional optical components. Also note that the present configuration of the invention is compact and is very similar to a standard conventional non-PM fiber based Michelson interferometer configuration, which can be easily modified to the present invention configuration.

Figure 8:
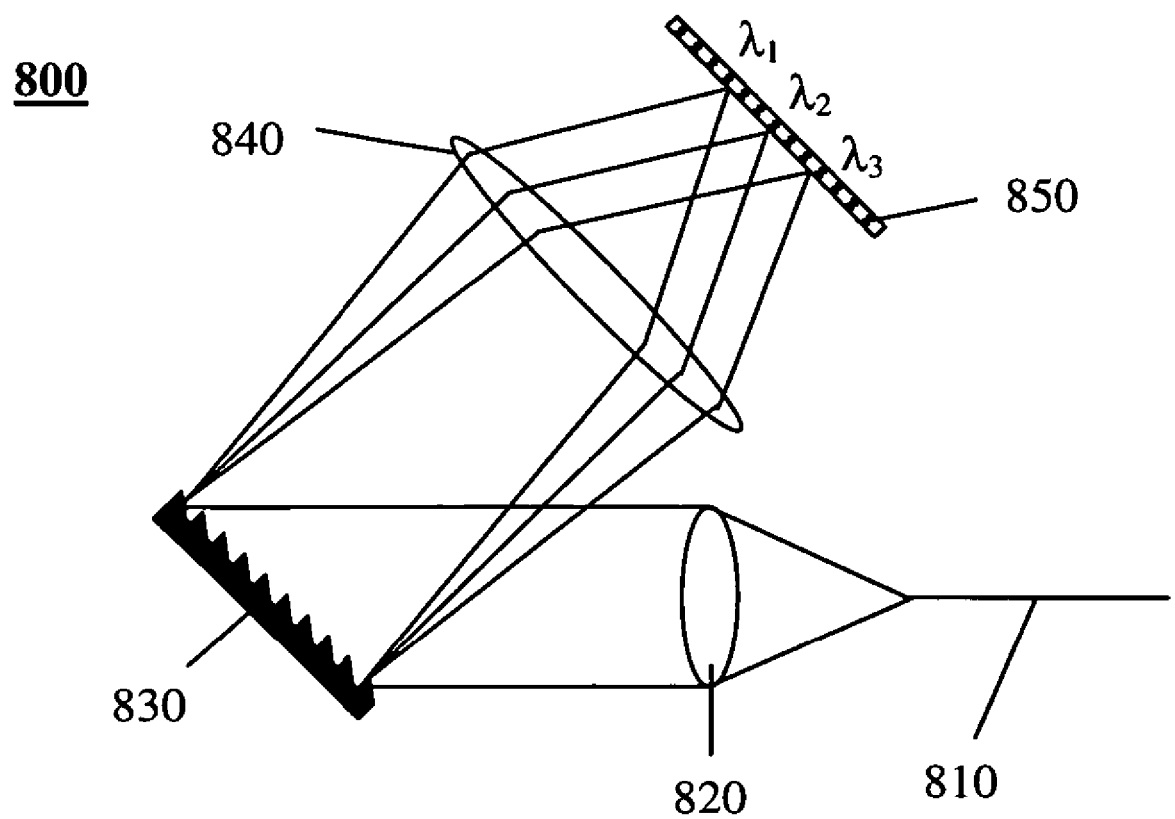
FIG. 8 shows an exemplary detection module particularly useful for spectral domain OCT, which is often polarization sensitive hence preferring a predetermined polarization state of the interfered optical waves.

It should also be understood that the present invention is particularly beneficial for application in spectral domain OCT (SD-OCT), as in such a case it is preferred that the polarization state of the interfering light waves sent to the detection module be fixed or predetermined as the module contains a polarization dependent optical element such as a grating. FIG. 8 shows an example of such a SD-OCT detection module. Assuming that the interfered light wave is guided in an optical fiber 810, a lens 820 can be used to collimate the beam and project it onto a blazed reflection grating 830. It is preferable that the optical fiber be short to minimize polarization effects in the fiber. The grating 830 will disperse the various wavelength components of the light source into parallel beams of different diffraction angles. It should be noted that while a blazed reflection grating has been shown here, other optical dispersing elements can be used to achieve the same goal. Some examples include a transmission grating, an arrayed waveguide grating, and a prism. Lens 840 can be used to focus the various beams of different diffraction angles and hence different wavelength components onto a detector array 850. Due to the fact that a fixed optical path length difference between a reference reflector and a sample reflection site will correspond to different optical phase delays for different wavelength components, the various wavelength components will hence give rise to alternating constructive and destructive interference fringe on the detector array 850. As a certain reflection site in the sample will lead to a certain spatial frequency of the interference fringe on the detector array, different reflection sites from the sample will hence result in interference fringes of different spatial frequencies. Consequently, a Fourier transform of the interference fringes of different spatial frequencies will provide information simultaneously on the various reflection sites of the sample. In such a case, the optical delay line does not need to be scanned.

Alternatively, the optical delay line may be used to achieve a phase shift modulation in order to determine the relative phase of the light returning from the reference and sample arm. One example of this is disclosed by Vakhtin et al. (Vakhtin, Andrei B. et al. (2003) "Differential spectral interferometry: an imaging technique for biomedical applications", Optics Letters, Volume 28, Issue 15, 1332–1334). Another example is given by Fercher (U.S. Pat. No. 6,377,349)

The foregoing description of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

References of Interest

The following references are incorporated herein by reference.

U.S Patent Documents

U.S. Pat. No. 5,202,745, Sorin, et al. "Polarization independent optical coherence-domain reflectometry"
U.S. Pat. No. 5,321,501, Swanson, et al. "Method and apparatus for optical imaging with means for controlling the longitudinal range of the sample"
U.S. Pat. No. 5,459,570, Swanson, et al. "Method and apparatus for performing optical measurements"
U.S. Pat. No. 6,111,645, Tearney, et al. "Grating based phase control optical delay line"
U.S. Pat. No. 6,282,011, Tearney, et al. "Grating based phase control optical delay line"
U.S. Pat. No. 6,377,349, Fercher, "Arrangement for spectral interferometric optical tomography and surface profile measurement"
U.S. Pat. No. 6,385,358, Everett M. et al. "Birefringence insensitive optical coherence domain reflectometry system"
U.S. Pat. No. 6,657,727, Izatt, et al. "Interferometers for optical coherence domain reflectometry and optical coherence tomography using nonreciprocal optical elements"

Other Publications

Fujimoto, J. G. et al. "Optical Coherence Tomography: An Emerging Technology for Biomedical Imaging and Optical Biopsy" *Neoplasia* (2000) 2, 9–25;
Fujimoto, J. G. "Optical coherence tomography for ultrahigh resolution in vivo imaging." *Nat Biotechnol* 21(11): 1361–7, (2003)
Huang, D., E. A. Swanson, et al. (1991). "Optical coherence tomography." *Science* 254 (5035): 1178–81
Kersey, A. D. et al. "Polarization-insensitive fiber optic Michelson interferometer", Electronics Letters, Volume: 27, Issue: 6, pages: 518–520, (1991)
Kobayashi et al, "Polarization-Independent Interferometric Optical-Time-Domain Reflectometer", 1991, J. Lightwave Tech. 9(5):623–628
Rollins A. M. et al. "Emerging Clinical Applications of Optical Coherence Tomography"Optics and Photonics News, Volume 13, Issue 4, 36–41, April 2002;
Rollins, A. M. and Izatt, J. A. "Optimal interferometer designs for optical coherence tomography" Optics Letters, Vol. 24 Issue 21 Page 1484 (1999)
Schmitt, J. M. "Optical coherence tomography (OCT): a review", IEEE Journal of Selected Topics in Quantum Electronics, Volume: 5, Issue: 4, Year: July/August 1999 pages:1205–1215;
Swanson E. A. et al. "Optical coherence tomography, Principles, instrumentation, and biological applications" Biomedical Optical Instrumentation and Laser-Assisted Biotechnology, A. M. Verga Scheggi et al. (eds.) pages: 291–303, 1996 Kluwer Academic Pulishers, Printed in the Netherlands
Vakhtin, Andrei B et al. "Differential spectral interferometry: an imaging technique for biomedical applications", 2003, Optics Letters, 28(15): 1332–1334
Youngquist et al., "Optical Coherence-Domain Reflectometry: A New Optical Evaluation Technique", 1987, Optics Letters 12(3):158–160

We claim:

1. An optical coherence domain reflectometry (OCDR) system comprising:
   a. a source arm with a light source;
   b. a polarizing beam splitter (PBS) having an input port optically connected to said source and two output ports;
   c. a non-polarizing beam splitter having an input port optically connected to an output port of said polarizing beam splitter, said non-polarizing beam splitter having two output ports;
   d. a sample arm leading to a sample, and optically connected to a first output port of said non-polarizing beam splitter;

e. a reference arm leading to a reflector, and optically connected to a second output port of said non-polarizing beam splitter;

f. a polarization manipulator for rotating the polarization of light waves returning from the sample and reference arms to an orthogonal direction, said polarization manipulator being defined by either a single element located in between said polarizing beam splitter and said non-polarizing beam splitter or by two elements, one each in said sample arm and reference arm respectively; and g. a detector collecting light combined by said non-polarizing beam splitter from said sample and reference arms, returned to said polarizing beam splitter in an orthogonal polarization state, and directed through a second output port of said polarizing beam splitter to a detector arm for interference signal detection and processing.

2. The OCDR system as in claim 1, wherein said sample is biological.

3. The OCDR system as in claim 1, wherein said sample is an eye.

4. The OCDR system as in claim 1, wherein said source and detector are coupled to said polarizing beam-splitter with a single mode fiber and the rest of the optical system is composed of bulk optics.

5. The OCDR system as in claim 1, wherein said sample arm includes a probe module having a one or two dimensional transverse scanning means to create an optical coherence tomography (OCT) system.

6. The OCDR system as in claim 1, wherein said detector arm includes an optical dispersive element and a detector array to create a spectral domain OCDR system.

7. The OCDR system as in claim 1, wherein said light source is a swept source with the center wavelength of a broadband optical radiation tunable over a certain range to create a swept source OCDR system.

8. The OCDR system as in claim 1, wherein said light source is polarized.

9. The OCDR system as in claim 1, wherein said light is unpolarized, and the light is polarized by said polarizing beam splitter.

10. The OCDR system as in claim 1, wherein said light source is optically connected to the polarizing beam splitter through a polarization controller.

11. The OCDR system as in claim 1, wherein said non-polarizing beam splitter couples more light into the sample arm than the reference arm to increase the optical efficiency of the system.

12. The OCDR system as in claim 1, wherein said sample arm includes a polarization controller for selecting a desired polarization direction of the light wave onto the sample.

13. The OCD system of claim 1, wherein at least one of the said sample arm or reference arm includes an optical fiber having an optical delay line for optical path length or optical phase modulation.

14. The OCDR system as in claim 1, wherein said polarization manipulator that rotates the returned light wave polarization to an orthogonal direction is a Faraday rotator with an optical rotation angle equal to 45°+M'90°, wherein M is an integer.

15. The OCDR system as in claim 1, wherein said polarization manipulator that rotates the returned light wave polarization to an orthogonal direction is a wave plate with an optical retardation substantially equal to $$\frac{\lambda}{4} + M\frac{\lambda}{2},$$

wherein M is an integer and $\lambda$ is the center wavelength of the light source.

16. The OCDR system as in claim 1, wherein said polarization manipulator is a wave plate with a retardation which when combined with the retardation of the sample provides a net quarter wave plate effect and hence to rotate the overall returned light wave polarization to an orthogonal direction.

17. The OCDR system as in claim 1, wherein said polarization manipulator that rotates the returned light wave polarization to an orthogonal direction is a dynamically controllable quarter wave plate.

18. The OCDR system as in claim 1, wherein said detector is a light detection module that is polarization sensitive and hence requires a fixed or predetermined polarization state of the arriving light waves.

19. The OCDR system as in claim 1, wherein said light source is a low coherence source.

20. A method for performing optical coherence domain reflectometry comprising the steps of:

a. guiding light from a light source through a polarizing beam splitter and a non-polarizing beam splitter and splitting the light into a sample arm leading to a sample, and a reference arm leading to a reflector;

b. combining the light waves returned from the sample arm and reference arm and guiding said light waves back to said polarizing beam splitter;

c. rotating the polarization direction of the returned light waves to an orthogonal direction prior to reentering the polarizing beam splitter; and d. at said polarizing beam splitter, channeling said combined and returned light waves having an orthogonal polarization direction to a detector arm for interference signal extraction and processing.

21. A method as recited in claim 20, wherein the step of rotating the polarization direction of the light waves is performed prior to the returned light being combined.

22. A method as recited in claim 20, wherein the step of rotating the polarization direction of the light waves is performed after the returned light is combined.

23. An optical coherence domain reflectometry (OCDR) system comprising:

a. a source arm with a light source;

b. a polarizing beam splitter (PBS) having an input port optically connected to said source and three output ports;

c. a sample arm leading to a sample, and optically connected to a first output port of said polarizing beam splitter;

d. a reference arm leading to a reflector, and optically connected to a second output port of said polarizing beam splitter;

e. a polarization manipulator for rotating the polarization of light waves returning from the sample and reference arms to an orthogonal direction, said polarization manipulator being defined by two elements, one each in said sample arm and reference arm respectively;

f. a detector collecting light combined by said polarizing beam splitter, returned from said sample and reference arms in an orthogonal polarization state, and directed through a third output port of said polarizing beam splitter to a detector arm for interference signal detection and processing; and g. a polarizer located in said detector arm prior to said detector and azimuthally oriented to extract an interference signal from the orthogonally polarized light from said sample and reference arms.

24. The OCDR system as in claim 23, wherein said sample is biological.

25. The OCDR system as in claim 23, wherein said sample is an eye.

26. The OCDR system as in claim 23, wherein said source and detector are coupled to said polarizing beam-splitter with a single mode fiber and the rest of the optical system is composed of bulk optics.

27. The OCDR system as in claim 23, wherein said sample arm includes a probe module having a one or two dimensional transverse scanning means to create an optical coherence tomography (OCT) system.

28. The OCDR system as in claim 23, wherein said detector arm includes an optical dispersive element and a detector array to create a spectral domain OCDR system.

29. The OCDR system as in claim 23, wherein said light source is a swept source with the center wavelength of a broadband optical radiation tunable over a certain range to create a swept source OCDR system.

30. The OCDR system as in claim 23, wherein said light source is polarized.

31. The OCDR system as in claim 23, wherein said light is unpolarized, and the light is polarized by a linear polarizer.

32. The OCDR system as in claim 23, wherein said light source is optically connected to said polarizing beam splitter through a polarization controller.

33. The OCDR system as in claim 23, wherein said polarizing beam splitter couples more light into the sample arm than the reference arm to increase the optical efficiency of the system.

34. The OCDR system as in claim 23, wherein said sample arm includes a polarization controller for selecting a desired polarization direction of the light wave onto the sample.

35. The OCDR system of claim 23, wherein at least one of the said sample arm or reference arm includes an optical fiber having an optical delay line for optical path length or optical phase modulation.

36. The OCDR system as in claim 23, wherein said polarization manipulator that rotates the returned light wave polarization to an orthogonal direction is a Faraday rotator with an optical rotation angle equal to 45°+M'90°, wherein M is an integer.

37. The OCDR system as in claim 23, wherein said polarization manipulator that rotates the returned light wave polarization to an orthogonal direction is a wave plate with an optical retardation substantially equal to $$\frac{\lambda}{4} + M\frac{\lambda}{2},$$

wherein M is an integer and λ is the center wavelength of the light source.

38. The OCDR system as in claim 23, wherein said polarization manipulator is a wave plate with a retardation which when combined with the retardation of the sample provides a net quarter wave plate effect and hence to rotate the overall returned light wave polarization to an orthogonal direction.

39. The OCDR system as in claim 23, wherein said polarization manipulator that rotates the returned light wave polarization to an orthogonal direction is a dynamically controllable quarter wave plate.

40. The OCDR system as in claim 23, wherein said detector is a light detection module that is polarization sensitive and hence requires a fixed or predetermined polarization state of the arriving light waves.

41. The OCDR system as in claim 23, wherein said light source is a low coherence source.

42. A method for performing optical coherence domain reflectometry comprising the steps of:

a. guiding light from a light source through a polarizing beam splitter and splitting light into a sample arm leading to a sample, and a reference arm leading to a reflector;

b. rotating the polarization direction of the returned light waves from said sample and reference reflector to an orthogonal direction prior to reentering the polarizing beam splitter;

c. at said polarizing beam splitter, combining the light waves returned from the sample arm and reference arm, and channeling said combined and returned light waves having an orthogonal polarization direction to a detector arm for interference signal extraction and processing; and;

d. in said detector arm, passing the combined light waves through a polarizer which is azimuthally oriented in a manner to extract an interference signal from the orthogonally polarized light from said sample and reference arms.

43. An apparatus for performing optical coherence domain reflectometry on a sample comprising:

a light source for generating a light beam;

a path splitter for dividing the beam into a first portion that travels along a sample path and a second portion that travels along a reference path, with the portions of said beam traveling down and back along said paths and then being recombined at said path splitter;

at least one detector for measuring the recombined beam and generating output signals that correspond to an interferometric response;

a polarizing beam splitter, said polarizing beam splitter being either functionally combined with the path splitter or being independent of the path splitter and located in the path of the light beam between the light source and the path splitter;

at least one polarization rotating element for rotating the polarization of the light beam after first passing through the polarizing beam splitter in a manner such that when the recombined beam returns to said polarizing beam splitter, the recombined beam will be redirected away from said light source and to the at least one detector; and a processor for evaluating the sample based on the output signals generated by the detector.

44. An apparatus as recited in claim 43, wherein said polarizing beam splitter and said path splitter are separate elements.

45. An apparatus as recited in claim 44, wherein said polarization rotating element is located between the polarizing beam splitter and the path splitter.

46. An apparatus as recited in claim 45, wherein said polarization rotating element is defined by a Faraday rotator.

47. An apparatus as recited in claim 46, wherein said polarization rotating element is defined by a wave plate.

48. An apparatus as recited in claim 43, including a pair of polarization rotating elements, one of said polarization rotating elements being located in said sample path and one of said elements being located in the reference path.

49. An apparatus as recited in claim 48, wherein said polarization rotating elements are defined by a Faraday rotator.

50. An apparatus as recited in claim 48, wherein said polarization rotating elements are defined by a wave plate.

51. An apparatus as recited in claim 50, wherein said polarizing beam splitter and said path splitter are functionally combined.

52. An apparatus as recited in claim 51, further including an analyzer between the polarizing beam splitter and the detector.

53. An apparatus as recited in claim 51, wherein said detector includes an optical dispersive element and a detector array for performing spectral domain detection.

54. An apparatus as recited in claim 43, wherein said sample path includes a beam scanner for creating a two or three-dimensional image of the sample.

55. An apparatus as recited in claim 43, further including an optical path length altering device associated with either the reference path or the sample path or both.

56. An apparatus as recited in claim 43, wherein the power splitting ratio of the path splitter is selected to direct a greater percentage of the beam power down the sample path.

57. An apparatus as recited in claim 43, wherein the power splitting ratio of the path splitter is selected to direct at least 70% of the beam power down the sample path.

58. An apparatus as recited in claim 43, wherein the sample is biological.

59. An apparatus as recited in claim 43, wherein the sample is an eye.

60. An apparatus as recited in claim 43, wherein the said sample path includes a polarization controller for selecting a desired polarization direction of the light beam onto the sample.

61. An apparatus as recited in claim 43, wherein the said polarization rotator is a wave plate with a retardation which when combined with the retardation of the sample provides a net quarter wave plate effect so as to rotate the overall returned light wave polarization to an orthogonal direction.

62. An apparatus as recited in claim 43, wherein said polarization rotator is a dynamically controllable quarter wave plate.

63. An apparatus as recited in claim 43, wherein said light source is a low coherence source.

64. An apparatus as recited in claim 43, further including a polarizer located between the polarizing beam splitter and the at least one detector and azimuthally oriented to extract an interference signal from the orthogonally polarized light from said sample and reference paths.

65. An apparatus as recited in claim 64, further including a second detector and wherein said polarizer is a second polarizing beam splitter for dividing the light between said at least one detector and said second detector, said detectors configured for balanced detection.

66. A method for performing optical coherence domain reflectometry on a sample comprising the steps of:
  a) generating a light beam;
  b) polarizing the beam;
  c) splitting the beam using a non-polarizing beam splitter into a first portion that travels along a sample path and a second portion that travels along a reference path, with the portions of said beam traveling down and back along said paths and then being recombined;
  d) rotating the polarization of the light portions returning from the sample and reference paths;
  e) redirecting the combined beam along a measurement path using a polarizing beam splitter separate from the non-polarizing beam splitter and wherein the non-polarizing beam splitter is located downstream from said polarizing beam splitter;
  f) measuring the recombined beam and generating output signals that correspond to an interferometric response; and
  g) evaluating the sample based on the generated output signals.

67. A method as recited in claim 66, wherein the step of rotating the polarization of the light is performed separately on both beam portions in their respective sample and reference paths.

68. A method as recited in claim 66, wherein the step of rotating the polarization of the light is performed separately on both beam portions in their respective sample and reference paths before the beam portions are recombined.

69. A method as recited in claim 66, wherein the step of rotating the polarization of the light portions occurs after the beams are recombined but before reaching the polarizing beam splitter.

* * * * *